United States Patent
Anastasio et al.

(10) Patent No.: US 6,521,747 B2
(45) Date of Patent: Feb. 18, 2003

(54) HAPLOTYPES OF THE AGTR1 GENE

(75) Inventors: Alison E. Anastasio, New Haven, CT (US); Kevin Finkel, Cheshire, CT (US); Beena Koshy, North Haven, CT (US); Helen Lee, Shelton, CT (US)

(73) Assignee: Genaissance Pharmaceuticals, Inc., New Haven, CT (US)

( * ) Notice: Subject to any disclaimer, the term of this patent is extended or adjusted under 35 U.S.C. 154(b) by 29 days.

(21) Appl. No.: 09/867,915

(22) Filed: May 30, 2001

(65) Prior Publication Data

US 2002/0182605 A1 Dec. 5, 2002

Related U.S. Application Data

(60) Provisional application No. 60/228,542, filed on Aug. 28, 2000.

(51) Int. Cl.[7] .................. C07H 21/02; C07H 21/04; C12Q 1/68; C12P 19/34
(52) U.S. Cl. .................. 536/23.1; 536/24.3; 536/22.1; 435/6; 435/91.2
(58) Field of Search .................. 435/6, 91.2; 536/23.1, 536/22.1, 24.3

(56) References Cited

PUBLICATIONS

Barnett, Anthony H., "The Role of Angiotensin II Receptor Antagonists in the Management of Diabetes," Blood Pressure, vol. 10, p. 21–26, (2001).

Bonnardeaux, A., Et Al., "Angiotensin II Type 1 Receptor Gene Polymorphisms in Human Essential Hypertension," Hypertension, vol. 24, p. 63–69, (1994).

Burnier & Maillard, "The Comparative Pharmacology of Angiotensin II Receptor Antagonists," Blood Pressure, vol. 10, p. 6–11, (2001).

Erdmann, J., Et Al., "Characterization of Polymorphisms in the Promoter of the Human Angiotensin II Subtype 1 (AT1) Receptor Gene," Ann. Human Genetics, vol. 63, p. 369–374, (1999).

Hernandez–Hernandez, R., Et Al., "Angiotensin II Receptor Antagonists in Arterial Hypertension," Journal of Human Hypertension, vol. 14, p. S69–S72, (2000).

Herzig, T.C., Et Al., "Angiotensin II Type 1a Receptor Gene Expression in the Heart: AP–1 and GATA–4 Participate in the Response to Pressure Overload," Proc. Natl. Acad. Sci. USA, vol. 94, (No. 14), p. 7543–7548, (1997).

Ito, M., Et Al., "Regulation of Blood Pressure by the Type 1A Angiotensin II Receptor Gene," Proc. Natl. Acad. Sci. (USA), vol. 92, (No. 5), p. 3521–3525, (1995).

Martin, M.N, Et Al., "Human Angiotensin II Type 1 Receptor Isoforms Encoded by Messenger RNA Splice Variants are Funcitonally Distinct," Mol. Endocrinology, vol. 15, (No. 2), p. 281–293, (2001).

Murphy, T.J., Et Al., "Isolation of a cDNA Encoding the Vascular Type–1 Angiotensin II Receptor," Nature, vol. 351, No. 6323, p. 233–236, (1991).

Nalogowska–Glosnicka, K., Et Al., "Angiotensin II Type 1 Receptor Gene A1166C Polymorphism is Associated with the Increased Risk of Pregnancy–Induced Hypertension," Medical Science Monitor, vol. 6, No. 3, p. 523–529, (2000).

Ramahi, T.M. Et Al., "Expanded Role for ARBs in Cardiovascular and Renal Disease? Recent Observations Have far–Reaching Implications," Postgraduate Medicine, vol. 109, (No. 4), p. 115–122, (2001).

Siragy, Helmy, "Angiotensin II Receptor Blockers: Review of the Binding Characteristics," The American Journal of Cardiology, vol. 84, (No. 10A), p. 3S–8S, (1999).

Takahashi, N. Et Al., "Association of a Polymorphism at the 5' Region of the Angiotensin II Type 1 Receptor with Hypertension," Ann. Hum. Genet., vol. 64, (No. 3), p. 197–205, (2000).

Wang, Wy Et Al., "Association of Angiotensin II Type 1 Receptor Gene Polymorphism with Essential Hypertension," Clinical Genetics, vol. 51, (No. 1), p. 31–43, (1997).

*Primary Examiner*—Jeffrey Fredman
(74) *Attorney, Agent, or Firm*—Sandra L. Shaner; Nathaniel D. Judisch; Melodie W. Henderson

(57) ABSTRACT

Novel genetic variants of the Angiotensin Receptor 1 (AGTR1) gene are described. Various genotypes, haplotypes, and haplotype pairs that exist in the general United States population are disclosed for the AGTR1 gene. Compositions and methods for haplotyping and/or genotyping the AGTR1 gene in an individual are also disclosed. Polynucleotides defined by the sequence of the haplotypes disclosed herein are also described.

32 Claims, 4 Drawing Sheets

POLYMORPHISMS IN THE AGTR1 GENE

```
TTAATGATAA ATGAATTGGT CCTGCTTACC TCAGGAAAAA CTTTCAAGTC
TTTCTGAAAA ACTAATTTAA TTCAGTAGTA TTTTCTAAGA TTTAGGTTAT     100
GTTTTTAATC AATTTGGAAA CCAAGATTTA CTTATAGAAA AAAAGGAAAA
         A
GGACCTAGAT AGGTTTATTC ACATAGAATC CCAATTTCAC TTCTCTGGAT     200
GATACCATTT TCTACAAAAG CAATTATGTT CTAAAATTTA AGTGTGCTTT
CTTAGGCTTT ATCAGTTCAC AGTGTTTCCT TAAGAAATAT GATCCAGTAT     300
TTTTTCCTAA GACTAAAGTT GAGTTACTAC GTTTATGACT GAGAAATGAA
                                                    T
TGTTTGTTAG TTTGTTTGTT TACAATAAGA ATTTTTTCTT TACCATTTTA     400
TTTTTATTTT CCCCAGGTGT ATTTGATATA GTGTTTGCAA CAAATTCGAC
CCAGGTGATC AAAATGATTC TCAACTCTTC TACTGAAGAT GGTATTAAAA     500
         [exon 1: 464..
GAATCCAAGA TGATTGTCCC AAAGCTGGAA GGCATAATTA CATATTTGTC
ATGATTCCTA CTTTATACAG TATCATCTTT GTGGTGGGAA TATTTGGAAA     600
CAGCTTGGTG GTGATAGTCA TTTACTTTTA TATGAAGCTG AAGACTGTGG
CCAGTGTTTT TCTTTTGAAT TTAGCACTGG CTGACTTATG CTTTTTACTG     700
ACTTTGCCAC TATGGGCTGT CTACACAGCT ATGGAATACC GCTGGCCCTT
TGGCAATTAC CTATGTAAGA TTGCTTCAGC CAGCGTCAGT TTCAACCTGT     800
ACGCTAGTGT GTTTCTACTC ACGTGTCTCA GCATTGATCG ATACCTGGCT
ATTGTTCACC CAATGAAGTC CCGCCTTCGA CGCACAATGC TTGTAGCCAA     900
AGTCACCTGC ATCATCATTT GGCTGCTGGC AGGCTTGGCC AGTTTGCCAG
CTATAATCCA TCGAAATGTA TTTTTCATTG AGAACACCAA TATTACAGTT    1000
TGTGCTTTCC ATTATGAGTC CCAAAATTCA ACCCTTCCGA TAGGGCTGGG
                                         C
CCTGACCAAA AATATACTGG GTTTCCTGTT TCCTTTTCTG ATCATTCTTA    1100
                  C
CAAGTTATAC TCTTATTTGG AAGGCCCTAA AGAAGGCTTA TGAAATTCAG
AAGAACAAAC CAAGAAATGA TGATATTTTT AAGATAATTA TGGCAATTGT    1200
GCTTTTCTTT TTCTTTTCCT GGATTCCCCA CCAAATATTC ACTTTTCTGG
ATGTATTGAT TCAACTAGGC ATCATACGTG ACTGTAGAAT TGCAGATATT    1300
GTGGACACGG CCATGCCTAT CACCATTTGT ATAGCTTATT TTAACAATTG
CCTGAATCCT CTTTTTTATG GCTTTCTGGG GAAAAAATTT AAAAGATATT    1400
TTCTCCAGCT TCTAAAATAT ATTCCCCCAA AAGCCAAATC CCACTCAAAC
CTTTCAACAA AAATGAGCAC GCTTTCCTAC CGCCCCTCAG ATAATGTAAG    1500
                T
CTCATCCACC AAGAAGCCTG CACCATGTTT TGAGGTTGAG TGACATGTTC
                             G
           ..1543]
GAAACCTGTC CATAAAGTAA TTTTGTGAAA GAAGGAGCAA GAGAACATTC    1600
CTCTGCAGCA CTTCACTACC AAATGAGCAT TAGCTACTTT TCAGAATTGA
                G
AGGAGAAAAT GCATTATGTG GACTGAACCG ACTTTTCTAA AGCTCTGAAC    1700
AAAAGCTTTT CTTTCCTTTT GCAACAAGAC AAAGCAAAGC CACATTTTGC
ATTAGACAGA TGACGGCTGC TCGAAGAACA ATGTCAGAAA CTCGATGAAT    1800
GTGTTGATTT GAGAAATTTT ACTGACAGAA ATGCAATCTC CCTAGCCTGC
TTTTGTCCTG TTATTTTTTA TTTCCACATA AAGGTATTTA GAATATATTA    1900
AATCGTTAGA GGAGCAACAG GAGATGAGAG TTCCAGATTG TTCTGTCCAG
TTTCCAAAGG GCAGTAAAGT TTTCGTGCCG GTTTTCAGCT ATTAGCAACT    2000
GCTGCTACAC TTGCACCTGG TACTGCACAT TTTGTACAAA GATATGCTAA
GCAGTAGTCG TCAAGTTGCA GATCTTTTTG TGAAATTCAA CCTGTGTCTT    2100
ATAGGTTTAC ACTGCCAAAA CAATGCCCGT AAGATGGCTT ATTTGTATAA
```

FIGURE 1A

```
TGGTGTTACT AAAGTCACAT ATAAAAGTTA AACTACTTGT AAAGGTGCTG      2200
CACTGGTCCC AAGTAGTAGT GTCTTCCTAG TATATTAGTT TGATTTAATA
TCTGAGAAGT GTATATAGTT TGTGGTAAAA AGATTATATA TCATAAAGTA      2300
TGCCTTCTGT TTAAAAAAAG TATATATCTA CACATATATA TATATGTATA
TCTATATCTC TAAACTGCTG TTAATTGATT AAAATCTGGC AAAGTTATAT      2400
TTACTTTAAA ATAAAATAAT TTTATTGCAA TGTATTTATC TTCATTACTT
AAAATAGATG CTAATTTATT TTAAAATAAG ACTACCTTGA ATGAGTATGA      2500
ATATATTTTT ATTTAAATTT TGATACAACT GATAGTTTAA TACTATTGGT
TATAGATTTT TTATCCTGAC ATTGAAAAGT TAAAGAAAAA ACATTTGTT       2600
CTACTGCATG TCATGGAATA AACACATCGT TT                         2632
```

FIGURE 1B

POLYMORPHISMS IN THE CODING SEQUENCE OF AGTR1

```
ATGATTCTCA ACTCTTCTAC TGAAGATGGT ATTAAAAGAA TCCAAGATGA
TTGTCCCAAA GCTGGAAGGC ATAATTACAT ATTTGTCATG ATTCCTACTT    100
TATACAGTAT CATCTTTGTG GTGGGAATAT TTGGAAACAG CTTGGTGGTG
ATAGTCATTT ACTTTTATAT GAAGCTGAAG ACTGTGGCCA GTGTTTTTCT    200
TTTGAATTTA GCACTGGCTG ACTTATGCTT TTTACTGACT TTGCCACTAT
GGGCTGTCTA CACAGCTATG GAATACCGCT GGCCCTTTGG CAATTACCTA    300
TGTAAGATTG CTTCAGCCAG CGTCAGTTTC AACCTGTACG CTAGTGTGTT
TCTACTCACG TGTCTCAGCA TTGATCGATA CCTGGCTATT GTTCACCCAA    400
TGAAGTCCCG CCTTCGACGC ACAATGCTTG TAGCCAAAGT CACCTGCATC
ATCATTTGGC TGCTGGCAGG CTTGGCCAGT TTGCCAGCTA TAATCCATCG    500
AAATGTATTT TTCATTGAGA ACACCAATAT TACAGTTTGT GCTTTCCATT
ATGAGTCCCA AAATTCAACC CTTCCGATAG GGCTGGGCCT GACCAAAAAT    600
                                 C
ATACTGGGTT TCCTGTTTCC TTTTCTGATC ATTCTTACAA GTTATACTCT
           C
TATTTGGAAG GCCCTAAAGA AGGCTTATGA AATTCAGAAG AACAAACCAA    700
GAAATGATGA TATTTTTAAG ATAATTATGG CAATTGTGCT TTTCTTTTTC
TTTTCCTGGA TTCCCCACCA AATATTCACT TTTCTGGATG TATTGATTCA    800
ACTAGGCATC ATACGTGACT GTAGAATTGC AGATATTGTG GACACGGCCA
TGCCTATCAC CATTTGTATA GCTTATTTTA CAATTGCCT GAATCCTCTT    900
TTTTATGGCT TTCTGGGGAA AAAATTTAAA AGATATTTTC TCCAGCTTCT
AAAATATATT CCCCCAAAAG CCAAATCCCA CTCAAACCTT TCAACAAAAA    1000
TGAGCACGCT TTCCTACCGC CCCTCAGATA ATGTAAGCTC ATCCACCAAG
     T
AAGCCTGCAC CATGTTTTGA GGTTGAGTGA                         1080
          G
```

FIGURE 2

ISOFORMS OF THE AGTR1 PROTEIN

```
MILNSSTEDG IKRIQDDCPK AGRHNYIFVM IPTLYSIIFV VGIFGNSLVV
IVIYFYMKLK TVASVFLLNL ALADLCFLLT LPLWAVYTAM EYRWPFGNYL   100
CKIASASVSF NLYASVFLLT CLSIDRYLAI VHPMKSRLRR TMLVAKVTCI
IIWLLAGLAS LPAIIHRNVF FIENTNITVC AFHYESQNST LPIGLGLTKN   200
ILGFLFPFLI ILTSYTLIWK ALKKAYEIQK NKPRNDDIFK IIMAIVLFFF
         S
FSWIPHQIFT FLDVLIQLGI IRDCRIADIV DTAMPITICI AYFNNCLNPL   300
FYGFLGKKFK RYFLQLLKYI PPKAKSHSNL STKMSTLSYR PSDNVSSSTK
                                         M
KPAPCFEVE                                                359
```

FIGURE 3

HAPLOTYPES OF THE AGTR1 GENE

RELATED APPLICATIONS

This application claims the benefit of U.S. Provisional application Ser. No. 60/228,542 filed Aug. 28, 2000.

FIELD OF THE INVENTION

This invention relates to variation in genes that encode pharmaceutically-important proteins. In particular, this invention provides genetic variants of the human angiotensin receptor 1 (AGTR1) gene and methods for identifying which variant(s) of this gene is/are possessed by an individual.

BACKGROUND OF THE INVENTION

Current methods for identifying pharmaceuticals to treat disease often start by identifying, cloning, and expressing an important target protein related to the disease. A determination of whether an agonist or antagonist is needed to produce an effect that may benefit a patient with the disease is then made. Then, vast numbers of compounds are screened against the target protein to find new potential drugs. The desired outcome of this process is a lead compound that is specific for the target, thereby reducing the incidence of the undesired side effects usually caused by activity at non-intended targets. The lead compound identified in this screening process then undergoes further in vitro and in vivo testing to determine its absorption, disposition, metabolism and toxicological profiles. Typically, this testing involves use of cell lines and animal models with limited, if any, genetic diversity.

What this approach fails to consider, however, is that natural genetic variability exists between individuals in any and every population with respect to pharmaceutically-important proteins, including the protein targets of candidate drugs, the enzymes that metabolize these drugs and the proteins whose activity is modulated by such drug targets. Subtle alteration(s) in the primary nucleotide sequence of a gene encoding a pharmaceutically-important protein may be manifested as significant variation in expression, structure and/or function of the protein. Such alterations may explain the relatively high degree of uncertainty inherent in the treatment of individuals with a drug whose design is based upon a single representative example of the target or enzyme (s) involved in metabolizing the drug. For example, it is well-established that some drugs frequently have lower efficacy in some individuals than others, which means such individuals and their physicians must weigh the possible benefit of a larger dosage against a greater risk of side effects. Also, there is significant variation in how well people metabolize drugs and other exogenous chemicals, resulting in substantial interindividual variation in the toxicity and/or efficacy of such exogenous substances (Evans et al., 1999, *Science* 286:487–491). This variability in efficacy or toxicity of a drug in genetically-diverse patients makes many drugs ineffective or even dangerous in certain groups of the population, leading to the failure of such drugs in clinical trials or their early withdrawal from the market even though they could be highly beneficial for other groups in the population. This problem significantly increases the time and cost of drug discovery and development, which is a matter of great public concern.

It is well-recognized by pharmaceutical scientists that considering the impact of the genetic variability of pharmaceutically-important proteins in the early phases of drug discovery and development is likely to reduce the failure rate of candidate and approved drugs (Marshall A 1997 *Nature Biotech* 15:1249–52; Kleyn P W et al. 1998 *Science* 281: 1820–21; Kola I 1999 *Curr Opin Biotech* 10:589–92; Hill A V S et al. 1999 *in Evolution in Health and Disease* Stearns S S (Ed.) Oxford University Press, New York, pp 62–76; Meyer U. A. 1999 *in Evolution in Health and Disease* Stearns S S (Ed.) Oxford University Press, New York, pp 41–49; Kalow W et al. 1999 *Clin. Pharm. Therap.* 66:445–7; Marshall, E 1999 *Science* 284:406–7; Judson R et al. 2000 *Pharmacogenomics* 1:1–12; Roses AD 2000 *Nature* 405:857–65). However, in practice this has been difficult to do, in large part because of the time and cost required for discovering the amount of genetic variation that exists in the population (Chakravarti A 1998 *Nature Genet* 19:216–7; Wang D G et al 1998 *Science* 280:1077–82; Chakravarti A 1999 *Nat Genet* 21:56–60 (suppl); Stephens J C 1999 *Mol. Diagnosis* 4:309–317; Kwok P Y and Gu S 1999 *Mol. Med. Today* 5:538–43; Davidson S 2000 *Nature Biotech* 18:1134–5).

The standard for measuring genetic variation among individuals is the haplotype, which is the ordered combination of polymorphisms in the sequence of each form of a gene that exists in the population. Because haplotypes represent the variation across each form of a gene, they provide a more accurate and reliable measurement of genetic variation than individual polymorphisms. For example, while specific variations in gene sequences have been associated with a particular phenotype such as disease susceptibility (Roses A D supra; Ulbrecht M et al. 2000 *Am J Respir Crit Care Med* 161: 469–74) and drug response (Wolfe C R et al. 2000 *BMJ* 320:987–90; Dahl BS 1997 *Acta Psychiatr Scand* 96 (Suppl 391): 14–21), in many other cases an individual polymorphism may be found in a variety of genomic backgrounds, i.e., different haplotypes, and therefore shows no definitive coupling between the polymorphism and the causative site for the phenotype (Clark A G et al. 1998 *Am J Hum Genet* 63:595–612; Ulbrecht M et al. 2000 supra; Drysdale et al. 2000 *PNAS* 97:10483–10488). Thus, there is an unmet need in the pharmaceutical industry for information on what haplotypes exist in the population for pharmaceutically-important genes. Such haplotype information would be useful in improving the efficiency and output of several steps in the drug discovery and development process, including target validation, identifying lead compounds, and early phase clinical trials (Marshall et al., supra).

One pharmaceutically-important gene for the treatment of hypertension is the angiotensin receptor 1 (AGTR1) gene or its encoded product. AGTR1 is a G protein-coupled receptor that binds to the vasopressor angiotensin II, which is an important effector controlling blood pressure and volume in the cardiovascular system. AGTR1 appears to mediate the major cardiovascular effects of angiotensin II, and this is accomplished through activation of a phosphatidylinositol-calcium second messenger system (Murphy et al., *Nature* 1991; 351:233–236).

Pharmacologic agents that antagonize AGTR1 have been shown to be highly successful in the treatment of angiotensin II-dependent hypertension (Ramahi, *Postgrad. Med* 2001; 109:115–122). This recently developed class of angiotensin II receptor blockers (ARBs) appear to be as effective as angiotensin-converting enzyme (ACE) inhibitors in delaying the progression of renal injury in animal models of diabetes (Barnett, *Blood Press* 2001; 10 Suppl 1:21–26). They act by selectively blocking the binding of angiotensin II to AGTR1 and may therefore offer a more complete blockade of the renin-angiotensin system than ACE inhibitors, which inhibit the conversion of angiotensin I to angiotensin II.

Unlike the angiotensin converting enzyme (ACE) inhibitors, these new drugs block the effects of angiotensin II regardless of whether it is produced systemically in the circulation or locally via ACE- or non-ACE-dependent pathways in tissues.

With the AGTR1 receptor blocked, angiotensin II is available to activate AGTR2, which mediates several potentially beneficial effects in the cardiovascular system, including vasodilation, antiproliferation, and apoptosis (Siragy, *Am J Cardiol.* 1999; 84:3S–8S). ARBs control a number of angiotensin II effects that are relevant to the pathophysiology of cardiovascular disease, including vasoconstriction, renal sodium reabsorption, aldosterone and vasopressin secretion, sympathetic activation, and vascular and cardiac hyperplasia and hypertrophy. Thus, ARBs provide a highly selective approach for regulating the effects of angiotensin II (Siragy, supra).

Most notable among ARBs is losartan, which has been found to be an effective anti-hypertension drug as it has an active metabolite that prolongs its duration of action. Other ARBs include valsartan, eprosartan, irbesartan, telmisartan, candesartan, and many others under investigation. Candesartan cilexetil requires conversion to an active form after administration. Telmisartan has the longest duration of action, with a terminal elimination half-life of around 24 hours in comparison with 11–15 hours for irbesartan, the agent with the next longest half-life (Burnier and Maillard, *Blood Press* 2001; 10 Suppl 1:6–11).

Therapy with any of the above drugs controls blood pressure in 40 to 50% of patients with mild to moderate hypertension. Tolerability has been reported to be very good, and ARBs would be a drug of choice in otherwise well-controlled hypertensive patients treated with angiotensin-converting enzyme inhibitors who developed cough or angioedema (Hernandez-Hernandez et al., *J Hum Hypertens.* 2000; 14 Suppl 1:S69–S72).

Angiotensin II has also been implicated in the development of cardiac hypertrophy, because ACE inhibitors and ARBs prevent or regress ventricular hypertrophy in animal models and in humans. Herzig et al. (*Proc. Natl. Acad. Sci. U.S.A* 1997; 94:7543–7548) studied AGTR1 promoter activity during cardiac hypertrophy, and discovered that AGTR1 expression is enhanced 160% in hypertrophied myocardium compared to normal myocardium, but that this effect could blocked by introducing mutations into either the AP-1 or GATA consensus binding sites within the AGTR1 promoter. These results suggest that the AP-1 and GATA consensus sites in the promoter regulate AGTR1 activity in cardiac muscle.

Several polymorphisms in the human AGTR1 gene have been discovered, some of which have been reported to be associated with hypertension. For example, Bonnardeaux et al. (*Hypertension* 1994; 24:63–69) identified an adenine or cytosine polymorphism (A1166C) located in the 3-prime untranslated region of the AGTR1 gene. This variant was present at a significantly elevated frequency in 206 Caucasian patients with essential hypertension. Wang et al. (*Clin Genet* 1997; 51:31–34) did a case-control study of the A1166C variant in a well-characterized group of 108 Caucasian hypertensive subjects with a strong family history (two affected parents) and early onset disease. The frequency of the A1166C allele in this subject group was 0.40 in hypertensives compared to 0.29 in normotensives. Further characterization of the A1629C polymorphism has shown it is significantly more frequent in women who develop pregnancy-induced hypertension as compared to healthy controls (Nalogowska-Glosnicka et al., *Med Sci. Monit.* 2000; 6:523–529). These data further support the notion that AGTR1 is an important target for the control of angiotensin II-dependent hypertension.

The angiotensin receptor 1 gene is located on chromosome 3q21–q25 and contains 1 exon that encodes a 359 amino acid protein. Two human AGTR1 subtypes have been identified, termed AGTR1A (FIG. 3) and AGTR1B, and recent evidence has indicated there may be as many four AGTR1 splice variants that are expressed in humans (Martin et al., *Mol. Endocrinol.* 2001; 15:281–293). AGTR1A and AGTR1B share substantial sequence homology and wide tissue distributions. AGTR1 seems to predominate in many tissues, but not in adrenal or anterior pituitary glands, and expression of the two types of receptors may be differentially regulated in the heart and the adrenals. This differential tissue distribution and regulation of AGTR1 subtypes may serve to modulate the biologic effects of angiotensin II (Ito et al., *Proc. Natl. Acad. Sci. U.S.A* 1995; 92:3521–3525). Reference sequences for the AGTR1 gene (Genaissance Reference No. 2506603; SEQ ID NO:1), coding sequence (GenBank Accession No:NM_000685.2), and protein are shown in FIGS. 1, 2 and 3, respectively.

Three additional known single nucleotide polymorphisms have been reported in the literature and correspond to thymine or cytosine at nucleotide position 1036 (NCBI SNP Database: Rs#5182), adenine or guanine at nucleotide position 1525 (NCBI SNP Database; Rs#5183), and thymine or guanine at nucleotide position 1613 (NCBI SNP Database; Rs#5185) in FIG. 1. Because of the potential for variation in the AGTR1 gene to affect the expression and function of the encoded protein, it would be useful to know whether additional polymorphisms exist in the AGTR1 gene, as well as how such polymorphisms are combined in different copies of the gene. Such information could be applied for studying the biological function of AGTR1 as well as in identifying drugs targeting this protein for the treatment of disorders related to its abnormal expression or function.

SUMMARY OF THE INVENTION

Accordingly, the inventors herein have discovered 4 novel polymorphic sites in the AGTR1 gene. These polymorphic sites (PS) correspond to the following nucleotide positions in FIG. 1: 104 (PS1), 348 (PS2), 1074 (PS4), and 1470 (PS5). The polymorphisms at these sites are thymine or adenine at PS1, guanine or thymine at PS2, thymine or cytosine at PS4, and cytosine or thymine at PS5. In addition, the inventors have determined the identity of the alleles at these sites, as well as at the previously identified sites at nucleotide positions 1036 (PS3), 1525 (PS6), and 1613 (PS7) in FIG. 1, in a human reference population of 79 unrelated individuals self-identified as belonging to one of four major population groups: African descent, Asian, Caucasian and Hispanic/Latino. From this information, the inventors deduced a set of haplotypes and haplotype pairs for PS 1–7 in the AGTR1 gene, which are shown below in Tables 5 and 4, respectively. Each of these AGTR1 haplotypes defines a naturally-occurring isoform (also referred to herein as an "isogene") of the AGTR1 gene that exists in the human population. The frequency with which each haplotype and haplotype pair occurs within the total reference population and within each of the four major population groups included in the reference population was also determined.

Thus, in one embodiment, the invention provides a method, composition and kit for genotyping the AGTR1 gene in an individual. The genotyping method comprises identifying the nucleotide pair that is present at one or more polymorphic sites selected from the group consisting of PS1, PS2, PS4, and PS5 in both copies of the AGTR1 gene from the individual. A genotyping composition of the invention comprises an oligonucleotide probe or primer which is designed to specifically hybridize to a target region containing, or adjacent to, one of these novel AGTR1 polymorphic sites. A genotyping kit of the invention comprises a set of oligonucleotides designed to genotype each of these novel AGTR1 polymorphic sites. In a preferred embodiment, the genotyping kit comprises a set of oligonucleotides designed to genotype each of PS 1–7. The genotyping method, composition, and kit are useful in determining whether an individual has one of the haplotypes in Table 5 below or has one of the haplotype pairs in Table 4 below.

The invention also provides a method for haplotyping the AGTR1 gene in an individual. In one embodiment, the haplotyping method comprises determining, for one copy of the AGTR1 gene, the identity of the nucleotide at one or more polymorphic sites selected from the group consisting of PS1, PS2, PS4, and PS5. In another embodiment, the haplotyping method comprises determining whether one copy of the individual's AGTR1 gene is defined by one of the AGTR1 haplotypes shown in Table 5, below, or a sub-haplotype thereof. In a preferred embodiment, the haplotyping method comprises determining whether both copies of the individual's AGTR1 gene are defined by one of the AGTR1 haplotype pairs shown in Table 4 below, or a sub-haplotype pair thereof. The method for establishing the AGTR1 haplotype or haplotype pair of an individual is useful for improving the efficiency and reliability of several steps in the discovery and development of drugs for treating diseases associated with AGTR1 activity, e.g., hypertension.

For example, the haplotyping method can be used by the pharmaceutical research scientist to validate AGTR1 as a candidate target for treating a specific condition or disease predicted to be associated with AGTR1 activity. Determining for a particular population the frequency of one or more of the individual AGTR1 haplotypes or haplotype pairs described herein will facilitate a decision on whether to pursue AGTR1 as a target for treating the specific disease of interest. In particular, if variable AGTR1 activity is associated with the disease, then one or more AGTR1 haplotypes or haplotype pairs will be found at a higher frequency in disease cohorts than in appropriately genetically matched controls. Conversely, if each of the observed AGTR1 haplotypes are of similar frequencies in the disease and control groups, then it may be inferred that variable AGTR1 activity has little, if any, involvement with that disease. In either case, the pharmaceutical research scientist can, without a priori knowledge as to the phenotypic effect of any AGTR1 haplotype or haplotype pair, apply the information derived from detecting AGTR1 haplotypes in an individual to decide whether modulating AGTR1 activity would be useful in treating the disease.

The claimed invention is also useful in screening for compounds targeting AGTR1 to treat a specific condition or disease predicted to be associated with AGTR1 activity. For example, detecting which of the AGTR1 haplotypes or haplotype pairs disclosed herein are present in individual members of a population with the specific disease of interest enables the pharmaceutical scientist to screen for a compound(s) that displays the highest desired agonist or antagonist activity for each of the most frequent AGTR1 isoforms present in the disease population. Thus, without requiring any a priori knowledge of the phenotypic effect of any particular AGTR1 haplotype or haplotype pair, the claimed haplotyping method provides the scientist with a tool to identify lead compounds that are more likely to show efficacy in clinical trials.

The method for haplotyping the AGTR1 gene in an individual is also useful in the design of clinical trials of candidate drugs for treating a specific condition or disease predicted to be associated with AGTR1 activity. For example, instead of randomly assigning patients with the disease of interest to the treatment or control group as is typically done now, determining which of the AGTR1 haplotype(s) disclosed herein are present in individual patients enables the pharmaceutical scientist to distribute AGTR1 haplotypes and/or haplotype pairs evenly to treatment and control groups, thereby reducing the potential for bias in the results that could be introduced by a larger frequency of an AGTR1 haplotype or haplotype pair that had a previously unknown association with response to the drug being studied in the trial. Thus, by practicing the claimed invention, the scientist can more confidently rely on the information learned from the trial, without first determining the phenotypic effect of any AGTR1 haplotype or haplotype pair.

In another embodiment, the invention provides a method for identifying an association between a trait and an AGTR1 genotype, haplotype, or haplotype pair for one or more of the novel polymorphic sites described herein. The method comprises comparing the frequency of the AGTR1 genotype, haplotype, or haplotype pair in a population exhibiting the trait with the frequency of the AGTR1 genotype or haplotype in a reference population. A higher frequency of the AGTR1 genotype, haplotype, or haplotype pair in the trait population than in the reference population indicates the trait is associated with the AGTR1 genotype, haplotype, or haplotype pair. In preferred embodiments, the trait is susceptibility to a disease, severity of a disease, the staging of a disease or response to a drug. In a particularly preferred embodiment, the AGTR1 haplotype is selected from the haplotypes shown in Table 5, or a sub-haplotype thereof. Such methods have applicability in developing diagnostic tests and therapeutic treatments for hypertension.

In yet another embodiment, the invention provides an isolated polynucleotide comprising a nucleotide sequence which is a polymorphic variant of a reference sequence for the AGTR1 gene or a fragment thereof. The reference sequence comprises SEQ ID NO:1 and the polymorphic variant comprises at least one polymorphism selected from the group consisting of adenine at PS1, thymine at PS2, cytosine at PS4, and thymine at PS5. In a preferred embodiment, the polymorphic variant comprises one or more additional polymorphisms selected from the group consisting of cytosine at PS3, guanine at PS6, and guanine at PS7.

A particularly preferred polymorphic variant is an isogene of the AGTR1 gene. An AGTR1 isogene of the invention comprises thymine or adenine at PS1, guanine or thymine at PS2, thymine or cytosine at PS3, thymine or cytosine at PS4, cytosine or thymine at PS5, adenine or guanine at PS6 and thymine or guanine at PS7. The invention also provides a collection of AGTR1 isogenes, referred to herein as an AGTR1 genome anthology.

In another embodiment, the invention provides a polynucleotide comprising a polymorphic variant of a reference sequence for an AGTR1 cDNA or a fragment thereof. The reference sequence comprises SEQ ID NO:2 (FIG. 2) and the polymorphic cDNA comprises at least one polymorphism selected from the group consisting of cytosine at a position corresponding to nucleotide 611 and thymine at a position corresponding to nucleotide 1007. In a preferred embodiment, the polymorphic variant comprises one or more additional polymorphisms selected from the group consisting of cytosine at a position corresponding to nucleotide 573 and guanine at a position corresponding to nucleotide 1062. A particularly preferred polymorphic cDNA variant comprises the coding sequence of an AGTR1 isogene defined by haplotypes 1–8 and 10.

Polynucleotides complementary to these AGTR1 genomic and cDNA variants are also provided by the invention. It is believed that polymorphic variants of the AGTR1 gene will be useful in studying the expression and function of AGTR1, and in expressing AGTR1 protein for use in screening for candidate drugs to treat diseases related to AGTR1 activity.

In other embodiments, the invention provides a recombinant expression vector comprising one of the polymorphic genomic variants operably linked to expression regulatory elements as well as a recombinant host cell transformed or transfected with the expression vector. The recombinant vector and host cell may be used to express AGTR1 for protein structure analysis and drug binding studies.

In yet another embodiment, the invention provides a polypeptide comprising a polymorphic variant of a reference amino acid sequence for the AGTR1 protein. The reference amino acid sequence comprises SEQ ID NO:3 (FIG. 3) and the polymorphic variant comprises at least one variant amino acid selected from the group consisting of serine at a position corresponding to amino acid position 204 and methionine at a position corresponding to amino acid position 336. A polymorphic variant of AGTR1 is useful in studying the effect of the variation on the biological activity of AGTR1 as well as on the binding affinity of candidate drugs targeting AGTR1 for the treatment of hypertension.

The present invention also provides antibodies that recognize and bind to the above polymorphic AGTR1 protein variant. Such antibodies can be utilized in a variety of diagnostic and prognostic formats and therapeutic methods.

The present invention also provides nonhuman transgenic animals comprising one of the AGTR1 polymorphic genomic variants described herein and methods for producing such animals. The transgenic animals are useful for studying expression of the AGTR1 isogenes in vivo, for in vivo screening and testing of drugs targeted against AGTR1 protein, and for testing the efficacy of therapeutic agents and compounds for hypertension in a biological system.

The present invention also provides a computer system for storing and displaying polymorphism data determined for the AGTR1 gene. The computer system comprises a computer processing unit; a display; and a database containing the polymorphism data. The polymorphism data includes the polymorphisms, the genotypes and the haplotypes identified for the AGTR1 gene in a reference population. In a preferred embodiment, the computer system is capable of producing a display showing AGTR1 haplotypes organized according to their evolutionary relationships.

BRIEF DESCRIPTION OF THE DRAWINGS

FIG. 1 illustrates a reference sequence for the AGTR1 gene (Genaissance Reference No. 2506603; contiguous lines; SEQ ID NO:1), with the start and stop positions of each region of coding sequence indicated with a bracket ([or]) and the numerical position below the sequence and the polymorphic site(s) and polymorphism(s) identified by Applicants in a reference population indicated by the variant nucleotide positioned below the polymorphic site in the sequence. SEQ ID NO:26 is equivalent to FIG. 1, with the two alternative allelic variants of each polymorphic site indicated by the appropriate nucleotide symbol (R=G or A, Y=T or C, M=A or C, K=G or T, S=G or C, and W=A or T; WIPO standard ST.25). SEQ ID NO:27 is a modified version of SEQ ID NO:26 that shows the context sequence of each polymorphic site 1–7 in a uniform format to facilitate electronic searching. For each polymorphic site, SEQ ID NO:27 contains a block of 60 bases of the nucleotide sequence encompassing the centrally-located polymorphic site at the $30^{th}$ position, followed by 60 bases of unspecified sequence to represent that each PS is separated by genomic sequence whose composition is defined elsewhere herein.

FIG. 2 illustrates a reference sequence for the AGTR1 coding sequence (contiguous lines; SEQ ID NO:2), with the polymorphic site(s) and polymorphism(s) identified by Applicants in a reference population indicated by the variant nucleotide positioned below the polymorphic site in the sequence.

FIG. 3 illustrates a reference sequence for the AGTR1 protein (contiguous lines; SEQ ID NO:3), with the variant amino acid(s) caused by the polymorphism(s) of FIG. 2 positioned below the polymorphic site in the sequence.

DESCRIPTION OF THE PREFERRED EMBODIMENTS

The present invention is based on the discovery of novel variants of the AGTR1 gene. As described in more detail below, the inventors herein discovered 10 isogenes of the AGTR1 gene by characterizing the AGTR1 gene found in genomic DNAs isolated from an Index Repository that contains immortalized cell lines from one chimpanzee and 93 human individuals. The human individuals included a reference population of 79 unrelated individuals self-identified as belonging to one of four major population groups: Caucasian (21 individuals), African descent (20 individuals), Asian (20 individuals), or Hispanic/Latino (18 individuals). To the extent possible, the members of this reference population were organized into population subgroups by their self-identified ethnogeographic origin as shown in Table 1 below.

TABLE 1

Population Groups in the Index Repository

| Population Group | Population Subgroup | No. of Individuals |
| --- | --- | --- |
| African descent | | 20 |
| | Sierra Leone | 1 |
| Asian | | 20 |
| | Burma | 1 |
| | China | 3 |
| | Japan | 6 |
| | Korea | 1 |
| | Philippines | 5 |
| | Vietnam | 4 |
| Caucasian | | 21 |
| | British Isles | 3 |
| | British Isles/Central | 4 |
| | British Isles/Eastern | 1 |
| | Central/Eastern | 1 |
| | Eastern | 3 |
| | Central/Mediterranean | 1 |

TABLE 1-continued

Population Groups in the Index Repository

| Population Group | Population Subgroup | No. of Individuals |
| --- | --- | --- |
| | Mediterranean | 2 |
| | Scandinavian | 2 |
| Hispanic/Latino | | 18 |
| | Caribbean | 8 |
| | Caribbean (Spanish Descent) | 2 |
| | Central American (Spanish Descent) | 1 |
| | Mexican American | 4 |
| | South American (Spanish Descent) | 3 |

In addition, the Index Repository contains three unrelated indigenous American Indians (one from each of North, Central and South America), one three-generation Caucasian family (from the CEPH Utah cohort) and one two-generation African-American family.

The AGTR1 isogenes present in the human reference population are defined by haplotypes for 7 polymorphic sites in the AGTR1 gene, 4 of which are believed to be novel. The AGTR1 polymorphic sites identified by the inventors are referred to as PS 1–7 to designate the order in which they are located in the gene (see Table 3 below), with the novel polymorphic sites referred to as PS 1, PS2, PS4, and PS5. Using the genotypes identified in the Index Repository for PS 1–7 and the methodology described in the Examples below, the inventors herein also determined the pair of haplotypes for the AGTR1 gene present in individual human members of this repository. The human genotypes and haplotypes found in the repository for the AGTR1 gene include those shown in Tables 4 and 5, respectively. The polymorphism and haplotype data disclosed herein are useful for validating whether AGTR1 is a suitable target for drugs to treat hypertension, screening for such drugs and reducing bias in clinical trials of such drugs.

In the context of this disclosure, the following terms shall be defined as follows unless otherwise indicated:

Allele—A particular form of a genetic locus, distinguished from other forms by its particular nucleotide sequence.

Candidate Gene—A gene which is hypothesized to be responsible for a disease, condition, or the response to a treatment, or to be correlated with one of these.

Gene—A segment of DNA that contains all the information for the regulated biosynthesis of an RNA product, including promoters, exons, introns, and other untranslated regions that control expression.

Genotype—An unphased 5' to 3' sequence of nucleotide pair(s) found at one or more polymorphic sites in a locus on a pair of homologous chromosomes in an individual. As used herein, genotype includes a full-genotype and/or a sub-genotype as described below.

Full-genotype—The unphased 5' to 3' sequence of nucleotide pairs found at all polymorphic sites examined herein in a locus on a pair of homologous chromosomes in a single individual.

Sub-genotype—The unphased 5' to 3' sequence of nucleotides seen at a subset of the polymorphic sites examined herein in a locus on a pair of homologous chromosomes in a single individual.

Genotyping—A process for determining a genotype of an individual.

Haplotype—A 5' to 3' sequence of nucleotides found at one or more polymorphic sites in a locus on a single chromosome from a single individual. As used herein, haplotype includes a full-haplotype and/or a sub-haplotype as described below.

Full-haplotype—The 5' to 3' sequence of nucleotides found at all polymorphic sites examined herein in a locus on a single chromosome from a single individual.

Sub-haplotype—The 5' to 3' sequence of nucleotides seen at a subset of the polymorphic sites examined herein in a locus on a single chromosome from a single individual.

Haplotype pair—The two haplotypes found for a locus in a single individual.

Haplotyping—A process for determining one or more haplotypes in an individual and includes use of family pedigrees, molecular techniques and/or statistical inference.

Haplotype data—Information concerning one or more of the following for a specific gene: a listing of the haplotype pairs in each individual in a population; a listing of the different haplotypes in a population; frequency of each haplotype in that or other populations, and any known associations between one or more haplotypes and a trait.

Isoform—A particular form of a gene, mRNA, cDNA or the protein encoded thereby, distinguished from other forms by its particular sequence and/or structure.

Isogene—One of the isoforms of a gene found in a population. An isogene contains all of the polymorphisms present in the particular isoform of the gene.

Isolated—As applied to a biological molecule such as RNA, DNA, oligonucleotide, or protein, isolated means the molecule is substantially free of other biological molecules such as nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

Locus—A location on a chromosome or DNA molecule corresponding to a gene or a physical or phenotypic feature.

Naturally-occurring—A term used to designate that the object it is applied to, e.g., naturally-occurring polynucleotide or polypeptide, can be isolated from a source in nature and which has not been intentionally modified by man.

Nucleotide pair—The nucleotides found at a polymorphic site on the two copies of a chromosome from an individual.

Phased—As applied to a sequence of nucleotide pairs for two or more polymorphic sites in a locus, phased means the combination of nucleotides present at those polymorphic sites on a single copy of the locus is known.

Polymorphic site (PS)—A position within a locus at which at least two alternative sequences are found in a population, the most frequent of which has a frequency of no more than 99%.

Polymorphic variant—A gene, mRNA, cDNA, polypeptide or peptide whose nucleotide or amino acid sequence varies from a reference sequence due to the presence of a polymorphism in the gene.

Polymorphism—The sequence variation observed in an individual at a polymorphic site. Polymorphisms include nucleotide substitutions, insertions, deletions and microsatellites and may, but need not, result in detectable differences in gene expression or protein function.

Polymorphism data—Information concerning one or more of the following for a specific gene: location of polymorphic sites; sequence variation at those sites; frequency of polymorphisms in one or more populations; the different genotypes and/or haplotypes determined for the gene; frequency of one or more of these genotypes and/or haplotypes in one or more populations; any known association(s) between a trait and a genotype or a haplotype for the gene.

Polymorphism Database—A collection of polymorphism data arranged in a systematic or methodical way and capable of being individually accessed by electronic or other means.

Polynucleotide—A nucleic acid molecule comprised of single-stranded RNA or DNA or comprised of complementary, double-stranded DNA.

Population Group—A group of individuals sharing a common ethnogeographic origin.

Reference Population—A group of subjects or individuals who are predicted to be representative of the genetic variation found in the general population. Typically, the reference population represents the genetic variation in the population at a certainty level of at least 85%, preferably at least 90%, more preferably at least 95% and even more preferably at least 99%.

Single Nucleotide Polymorphism (SNP)—Typically, the specific pair of nucleotides observed at a single polymorphic site. In rare cases, three or four nucleotides may be found.

Subject—A human individual whose genotypes or haplotypes or response to treatment or disease state are to be determined.

Treatment—A stimulus administered internally or externally to a subject.

Unphased—As applied to a sequence of nucleotide pairs for two or more polymorphic sites in a locus, unphased means the combination of nucleotides present at those polymorphic sites on a single copy of the locus is not known.

As discussed above, information on the identity of genotypes and haplotypes for the AGTR1 gene of any particular individual as well as the frequency of such genotypes and haplotypes in any particular population of individuals is expected to be useful for a variety of drug discovery and development applications. Thus, the invention also provides compositions and methods for detecting the novel AGTR1 polymorphisms and haplotypes identified herein.

The compositions comprise at least one AGTR1 genotyping oligonucleotide. In one embodiment, an AGTR1 genotyping oligonucleotide is a probe or primer capable of hybridizing to a target region that is located close to, or that contains, one of the novel polymorphic sites described herein. As used herein, the term "oligonucleotide" refers to a polynucleotide molecule having less than about 100 nucleotides. A preferred oligonucleotide of the invention is 10 to 35 nucleotides long. More preferably, the oligonucleotide is between 15 and 30, and most preferably, between 20 and 25 nucleotides in length. The exact length of the oligonucleotide will depend on many factors that are routinely considered and practiced by the skilled artisan. The oligonucleotide may be comprised of any phosphorylation state of ribonucleotides, deoxyribonucleotides, and acyclic nucleotide derivatives, and other functionally equivalent derivatives. Alternatively, oligonucleotides may have a phosphate-free backbone, which may be comprised of linkages such as carboxymethyl, acetamidate, carbamate, polyamide (peptide nucleic acid (PNA)) and the like (Varma, R. in Molecular Biology and Biotechnology, A Comprehensive Desk Reference, Ed. R. Meyers, VCH Publishers, Inc. (1995), pages 617–620). Oligonucleotides of the invention may be prepared by chemical synthesis using any suitable methodology known in the art, or may be derived from a biological sample, for example, by restriction digestion. The oligonucleotides may be labeled, according to any technique known in the art, including use of radiolabels, fluorescent labels, enzymatic labels, proteins, haptens, antibodies, sequence tags and the like.

Genotyping oligonucleotides of the invention must be capable of specifically hybridizing to a target region of an AGTR1 polynucleotide, i.e., an AGTR1 isogene. As used herein, specific hybridization means the oligonucleotide forms an anti-parallel double-stranded structure with the target region under certain hybridizing conditions, while failing to form such a structure when incubated with a non-target region or a, non-AGTR1 polynucleotide under the same hybridizing conditions. Preferably, the oligonucleotide specifically hybridizes to the target region under conventional high stringency conditions. The skilled artisan can readily design and test oligonucleotide probes and primers suitable for detecting polymorphisms in the AGTR1 gene using the polymorphism information provided herein in conjunction with the known sequence information for the AGTR1 gene and routine techniques.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, by Sambrook J. et al., in Molecular Cloning, A Laboratory Manual, $2^{nd}$ Edition, Cold Spring Harbor Press, Cold Spring Harbor, N.Y. (1989) and by Haymes, B. D. et al. in Nucleic Acid Hybridization, A Practical Approach, IRL Press, Washington, D.C. (1985). While perfectly complementary oligonucleotides are preferred for detecting polymorphisms, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the oligonucleotide probe or primer as long as the resulting probe or primer is still capable of specifically hybridizing to the target region.

Preferred genotyping oligonucleotides of the invention are allele-specific oligonucleotides. As used herein, the term allele-specific oligonucleotide (ASO) means an oligonucleotide that is able, under sufficiently stringent conditions, to hybridize specifically to one allele of a gene, or other locus, at a target region containing a polymorphic site while not hybridizing to the corresponding region in another allele(s). As understood by the skilled artisan, allele-specificity will depend upon a variety of readily optimized stringency conditions, including salt and formamide concentrations, as well as temperatures for both the hybridization and washing steps. Examples of hybridization and washing conditions typically used for ASO probes are found in Kogan et al., "Genetic Prediction of Hemophilia A" in PCR Protocols, A Guide to Methods and Applications, Academic Press, 1990 and Ruaño et al., 87 Proc. Natl. Acad. Sci. USA 6296–6300, 1990. Typically, an ASO will be perfectly complementary to one allele while containing a single mismatch for another allele.

Allele-specific oligonucleotides of the invention include ASO probes and ASO primers. ASO probes which usually provide good discrimination between different alleles are those in which a central position of the oligonucleotide probe aligns with the polymorphic site in the target region (e.g., approximately the $7^{th}$ or $8^{th}$ position in a 15mer, the $8^{th}$ or $9^{th}$ position in a 16mer, and the $10^{th}$ or $11^{th}$ position in a 20mer). An ASO primer of the invention has a 3' terminal nucleotide, or preferably a 3' penultimate nucleotide, that is complementary to only one nucleotide of a particular SNP, thereby acting as a primer for polymerase-mediated extension only if the allele containing that nucleotide is present. ASO probes and primers hybridizing to either the coding or noncoding strand are contemplated by the invention.

ASO probes and primers listed below use the appropriate nucleotide symbol (R=G or A, Y=T or C, M=A or C, K=G or T, S=G or C, and W=A or T; WIPO standard ST.25) at the position of the polymorphic site to represent the two alternative allelic variants observed at that polymorphic site.

A preferred ASO probe for detecting AGTR1 gene polymorphisms comprises a nucleotide sequence, listed 5', to 3', selected from the group consisting of:

TTATGTTWTTAATCA (SEQ ID NO:4) and its complement,

GAGAAATKAATGTTT (SEQ ID NO:5) and its complement,

CTGGGTTYCCTGTTT (SEQ ID NO:6) and its complement, and

ATGAGCAYGCTTTCC (SEQ ID NO:7) and its complement.

A preferred ASO primer for detecting AGTR1 gene polymorphisms comprises a nucleotide sequence, listed 5' to 3', selected from the group consisting of:

TTTAGGTTATGTTWT (SEQ ID NO:8); CCAAAT-TGATTAAWA (SEQ ID NO:9);

ATGACTGAGAAATKA (SEQ ID NO:10); ACTAA-CAAACATTMA (SEQ ID NO:11);

AATATACTGGGTTYC (SEQ ID NO:12); AAAAG-GAAACAGGRA (SEQ ID NO:13);

ACAAAAATGAGCAYG (SEQ ID NO:14); and GCGG-TAGGAAAGCRT (SEQ ID NO:15).

Other genotyping oligonucleotides of the invention hybridize to a target region located one to several nucleotides downstream of one of the novel polymorphic sites identified herein. Such oligonucleotides are useful in polymerase-mediated primer extension methods for detecting one of the novel polymorphisms described herein and therefore such genotyping oligonucleotides are referred to herein as "primer-extension oligonucleotides". In a preferred embodiment, the 3'-terminus of a primer-extension oligonucleotide is a deoxynucleotide complementary to the nucleotide located immediately adjacent to the polymorphic site.

A particularly preferred oligonucleotide primer for detecting AGTR1 gene polymorphisms by primer extension terminates in a nucleotide sequence, listed 5' to 3', selected from the group consisting of:

AGGTTATGTT (SEQ ID NO:16); AATTGATTAA (SEQ ID NO:17);

ACTGAGAAAT (SEQ ID NO:18); AACAAACATT (SEQ ID NO:19);

ATACTGGGTT (SEQ ID NO:20); AGGAAACAGG (SEQ ID NO:21);

AAAATGAGCA (SEQ ID NO:22); and GTAGGAAAGC (SEQ ID NO:23).

In some embodiments, a composition contains two or more differently labeled genotyping oligonucleotides for simultaneously probing the identity of nucleotides at two or more polymorphic sites. It is also contemplated that primer compositions may contain two or more sets of allele-specific primer pairs to allow simultaneous targeting and amplification of two or more regions containing a polymorphic site.

AGTR1 genotyping oligonucleotides of the invention may also be immobilized on or synthesized on a solid surface such as a microchip, bead, or glass slide (see, e.g., WO 98/20020 and WO 98/20019). Such immobilized genotyping oligonucleotides may be used in a variety of polymorphism detection assays, including but not limited to probe hybridization and polymerase extension assays. Immobilized AGTR1 genotyping oligonucleotides of the invention may comprise an ordered array of oligonucleotides designed to rapidly screen a DNA sample for polymorphisms in multiple genes at the same time.

In another embodiment, the invention provides a kit comprising at least two genotyping oligonucleotides packaged in separate containers. The kit may also contain other components such as hybridization buffer (where the oligonucleotides are to be used as a probe) packaged in a separate container. Alternatively, where the oligonucleotides are to be used to amplify a target region, the kit may contain, packaged in separate containers, a polymerase and a reaction buffer optimized for primer extension mediated by the polymerase, such as PCR.

The above described oligonucleotide compositions and kits are useful in methods for genotyping and/or haplotyping the AGTR1 gene in an individual. As used herein, the terms "AGTR1 genotype" and "AGTR1 haplotype" mean the genotype or haplotype contains the nucleotide pair or nucleotide, respectively, that is present at one or more of the novel polymorphic sites described herein and may optionally also include the nucleotide pair or nucleotide present at one or more additional polymorphic sites in the AGTR1 gene. The additional polymorphic sites may be currently known polymorphic sites or sites that are subsequently discovered.

One embodiment of the genotyping method involves isolating from the individual a nucleic acid sample comprising the two copies of the AGTR1 gene, or a fragment thereof, that are present in the individual, and determining the identity of the nucleotide pair at one or more polymorphic sites selected from the group consisting of PS1, PS2, PS4, and PS5 in the two copies to assign an AGTR1 genotype to the individual. As will be readily understood by the skilled artisan, the two "copies" of a gene in an individual may be the same allele or may be different alleles. In a preferred embodiment of the genotyping method, the identity of the nucleotide pair at one or more of the polymorphic sites selected from the group consisting of PS3, PS6, and PS7 is also determined. In a particularly preferred embodiment, the genotyping method comprises determining the identity of the nucleotide pair at each of PS1–7.

Typically, the nucleic acid sample is isolated from a biological sample taken from the individual, such as a blood sample or tissue sample. Suitable tissue samples include whole blood, semen, saliva, tears, urine, fecal material, sweat, buccal, skin and hair. The nucleic acid sample may be comprised of genomic DNA, mRNA, or cDNA and, in the latter two cases, the biological sample must be obtained from a tissue in which the AGTR1 gene is expressed. Furthermore it will be understood by the skilled artisan that mRNA or cDNA preparations would not be used to detect polymorphisms located in introns or in 5' and 3' untranslated regions. If an AGTR1 gene fragment is isolated, it must contain the polymorphic site(s) to be genotyped.

One embodiment of the haplotyping method comprises isolating from the individual a nucleic acid sample containing only one of the two copies of the AGTR1 gene, or a fragment thereof, that is present in the individual and determining in that copy the identity of the nucleotide at one or more polymorphic sites selected from the group consisting of PS1, PS2, PS4, and PS5 in that copy to assign an AGTR1 haplotype to the individual. The nucleic acid may be isolated using any method capable of separating the two copies of the AGTR1 gene or fragment such as one of the methods described above for preparing AGTR1 isogenes, with targeted in vivo cloning being the preferred approach. As will be readily appreciated by those skilled in the art, any individual clone will only provide haplotype information on one of the two AGTR1 gene copies present in an individual. If haplotype information is desired for the individual's other copy, additional AGTR1 clones will need to be examined. Typically, at least five clones should be examined to have more than a 90% probability of haplotyping both copies of the AGTR1 gene in an individual. In some embodiments, the haplotyping method also comprises identifying the nucleotide at one or more polymorphic sites selected from the group consisting of PS3, PS6, and PS7. In a particularly preferred embodiment, the nucleotide at each of PS 1–7 is identified.

In another embodiment, the haplotyping method comprises determining whether an individual has one or more of the AGTR1 haplotypes shown in Table 5. This can be accomplished by identifying, for one or both copies of the individual's AGTR1 gene, the phased sequence of nucleotides present at each of PS1–7. The present invention also contemplates that typically only a subset of PS 1–7 will need to be directly examined to assign to an individual one or more of the haplotypes shown in Table 5. This is because at least one polymorphic site in a gene is frequently in strong linkage disequilibrium with one or more other polymorphic sites in that gene (Drysdale, C M et al. 2000 *PNAS* 97:10483–10488; Rieder M J et al. 1999 *Nature Genetics* 22:59–62). Two sites are said to be in linkage disequilibrium if the presence of a particular variant at one site enhances the predictability of another variant at the second site (Stephens, J C 1999, *Mol. Diag.* 4:309–317). Techniques for determining whether any two polymorphic sites are in linkage disequilibrium are well-known in the art (Weir B. S. 1996 *Genetic Data Analysis II*, Sinauer Associates, Inc. Publishers, Sunderland, Mass.).

In a preferred embodiment, an AGTR1 haplotype pair is determined for an individual by identifying the phased sequence of nucleotides at one or more polymorphic sites selected from the group consisting of PS1, PS2, PS4, and PS5 in each copy of the AGTR1 gene that is present in the individual. In a particularly preferred embodiment, the haplotyping method comprises identifying the phased sequence of nucleotides at each of PS1–7 in each copy of the AGTR1 gene. When haplotyping both copies of the gene, the identifying step is preferably performed with each copy of the gene being placed in separate containers. However, it is also envisioned that if the two copies are labeled with different tags, or are otherwise separately distinguishable or identifiable, it could be possible in some cases to perform the method in the same container. For example, if first and second copies of the gene are labeled with different first and second fluorescent dyes, respectively, and an allele-specific oligonucleotide labeled with yet a third different fluorescent dye is used to assay the polymorphic site(s), then detecting a combination of the first and third dyes would identify the polymorphism in the first gene copy while detecting a combination of the second and third dyes would identify the polymorphism in the second gene copy.

In both the genotyping and haplotyping methods, the identity of a nucleotide (or nucleotide pair) at a polymorphic site(s) may be determined by amplifying a target region(s) containing the polymorphic site(s) directly from one or both copies of the AGTR1 gene, or a fragment thereof, and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

The target region(s) may be amplified using any oligonucleotide-directed amplification method, including but not limited to polymerase chain reaction (PCR) (U.S. Pat. No. 4,965,188), ligase chain reaction (LCR) (Barany et al., *Proc. Natl. Acad. Sci. USA* 88:189–193, 1991; WO90/01069), and oligonucleotide ligation assay (OLA) (Landegren et al., *Science* 241:1077–1080, 1988). Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et al., *Proc. Natl. Acad. Sci. USA* 89:392–396, 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs. Preferably, the members of the set have melting temperatures within 5° C., and more preferably within 2° C., of each other when hybridizing to each of the polymorphic sites being detected.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype or haplotype for the AGTR1 gene of an individual may also be determined by hybridization of a nucleic acid sample containing one or both copies of the gene, or fragment(s) thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the E. coli mutS protein (Modrich, P. Ann. Rev. Genet. 25:229–253, 1991). Alternatively, variant alleles can be identified by single strand conformation polymorphism (SSCP) analysis (Orita et al., Genomics 5:874–879, 1989; Humphries et al., in Molecular Diagnosis of Genetic Diseases, R. Elles, ed., pp. 321–340, 1996) or denaturing gradient gel electrophoresis (DGGE) (Wartell et al., Nuci. Acids Res. 18:2699–2706, 1990; Sheffield et al., Proc. Nati. Acad. Sci. USA 86:232–236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524. Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruaño et al., Nucl. Acids Res. 17:8392, 1989; Ruaño et al., Nucl. Acids Res. 19, 6877–6882, 1991; WO 93/22456; Turki et al., J Clin. Invest. 95:1635–1641, 1995). In addition, multiple polymorphic sites may be investigated by simultaneously amplifying multiple regions of the nucleic acid using sets of allele-specific primers as described in Wallace et al. (WO89/10414).

In addition, the identity of the allele(s) present at any of the novel polymorphic sites described herein may be indirectly determined by genotyping another polymorphic site that is in linkage disequilibrium with the polymorphic site that is of interest. Polymorphic sites in linkage disequilibrium with the presently disclosed polymorphic sites may be located in regions of the gene or in other genomic regions not examined herein. Genotyping of a polymorphic site in linkage disequilibrium with the novel polymorphic sites described herein may be performed by, but is not limited to, any of the above-mentioned methods for detecting the identity of the allele at a polymorphic site.

In another aspect of the invention, an individual's AGTR1 haplotype pair is predicted from its AGTR1 genotype using information on haplotype pairs known to exist in a reference population. In its broadest embodiment, the haplotyping prediction method comprises identifying an AGTR1 genotype for the individual at two or more AGTR1 polymorphic sites described herein, enumerating all possible haplotype pairs which are consistent with the genotype, accessing data containing AGTR1 haplotype pairs identified in a reference population, and assigning a haplotype pair to the individual that is consistent with the data. In one embodiment, the reference haplotype pairs include the AGTR1 haplotype pairs shown in Table 4.

Generally, the reference population should be composed of randomly-selected individuals representing the major ethnogeographic groups of the world. A preferred reference population for use in the methods of the present invention comprises an approximately equal number of individuals from Caucasian, African-descent, Asian and Hispanic-Latino population groups with the minimum number of each group being chosen based on how rare a haplotype one wants to be guaranteed to see. For example, if one wants to have a q% chance of not missing a haplotype that exists in the population at a p% frequency of occurring in the reference population, the number of individuals (n) who must be sampled is given by $2n=\log(1-q)/\log(1-p)$ where p and q are expressed as fractions. A preferred reference population allows the detection of any haplotype whose frequency is at least 10% with about 99% certainty and comprises about 20 unrelated individuals from each of the four population groups named above. A particularly preferred reference population includes a 3-generation family representing one or more of the four population groups to serve as controls for checking quality of haplotyping procedures.

In a preferred embodiment, the haplotype frequency data for each ethnogeographic group is examined to determine whether it is consistent with Hardy-Weinberg equilibrium. Hardy-Weinberg equilibrium (D. L. Hartl et al., Principles of Population Genomics, Sinauer Associates (Sunderland, Mass.), $3^{rd}$ Ed., 1997) postulates that the frequency of finding the haplotype pair $H_1/H_2$ is equal to $P_{H-W}(H_1/H_2)=2p(H_1)p(H_2)$ if $H_1 \neq H_2$ and $P_{H-W}(H_1/H_2)=p(H_1)p(H_2)$ if $H_1=H_2$. A statistically significant difference between the observed and expected haplotype frequencies could be due to one or more factors including significant inbreeding in the population group, strong selective pressure on the gene, sampling bias, and/or errors in the genotyping process. If large deviations from Hardy-Weinberg equilibrium are observed in an ethnogeographic group, the number of individuals in that group can be increased to see if the deviation is due to a sampling bias. If a larger sample size does not reduce the difference between observed and expected haplotype pair frequencies, then one may wish to consider haplotyping the individual using a direct haplotyping method such as, for example, CLASPER System™ technology (U.S. Pat. No. 5,866,404), single molecule dilution, or allele-specific long-range PCR (Michalotos-Beloin et al., Nucleic Acids Res. 24:4841–4843, 1996).

In one embodiment of this method for predicting an AGTR1 haplotype pair for an individual, the assigning step involves performing the following analysis. First, each of the possible haplotype pairs is compared to the haplotype pairs in the reference population. Generally, only one of the haplotype pairs in the reference population matches a possible haplotype pair and that pair is assigned to the individual. Occasionally, only one haplotype represented in the reference haplotype pairs is consistent with a possible haplotype pair for an individual, and in such cases the individual is assigned a haplotype pair containing this known haplotype and a new haplotype derived by subtracting the known haplotype from the possible haplotype pair. In rare cases, either no haplotypes in the reference population are consistent with the possible haplotype pairs, or alternatively, multiple reference haplotype pairs are consistent with the possible haplotype pairs. In such cases, the individual is preferably haplotyped using a direct molecular haplotyping method such as, for example, CLASPER System™ technology (U.S. Pat. No. 5,866,404), SMD, or allele-specific long-range PCR (Michalotos-Beloin et al., supra). A preferred process for predicting AGTR1 haplotype pairs from AGTR1 genotypes is described in U.S. Provisional Application Serial No. 60/198,340 and the corresponding International Application filed Apr. 18, 2001.

The invention also provides a method for determining the frequency of an AGTR1 genotype, haplotype, or haplotype pair in a population. The method comprises, for each member of the population, determining the genotype or the haplotype pair for the novel AGTR1 polymorphic sites described herein, and calculating the frequency any particular genotype, haplotype, or haplotype pair is found in the population. The population may be a reference population, a family population, a same sex population, a population group, or a trait population (e.g., a group of individuals exhibiting a trait of interest such as a medical condition or response to a therapeutic treatment).

In another aspect of the invention, frequency data for AGTR1 genotypes, haplotypes, and/or haplotype pairs are determined in a reference population and used in a method for identifying an association between a trait and an AGTR1 genotype, haplotype, or haplotype pair. The trait may be any detectable phenotype, including but not limited to susceptibility to a disease or response to a treatment. The method involves obtaining data on the frequency of the genotype(s), haplotype(s), or haplotype pair(s) of interest in a reference population as well as in a population exhibiting the trait. Frequency data for one or both of the reference and trait populations may be obtained by genotyping or haplotyping each individual in the populations using one of the methods described above. The haplotypes for the trait population may be determined directly or, alternatively, by the predictive genotype to haplotype approach described above. In another embodiment, the frequency data for the reference and/or trait populations is obtained by accessing previously determined frequency data, which may be in written or electronic form. For example, the frequency data may be present in a database that is accessible by a computer. Once the frequency data is obtained, the frequencies of the genotype(s), haplotype(s), or haplotype pair(s) of interest in the reference and trait populations are compared. In a preferred embodiment, the frequencies of all genotypes, haplotypes, and/or haplotype pairs observed in the populations are compared. If a particular AGTR1 genotype, haplotype, or haplotype pair is more frequent in the trait population than in the reference population at a statistically significant amount, then the trait is predicted to be associated with that AGTR1 genotype, haplotype or haplotype pair. Preferably, the AGTR1 genotype, haplotype, or haplotype pair being compared in the trait and reference populations is selected from the full-genotypes and full-haplotypes shown in Tables 4 and 5, or from sub-genotypes and sub-haplotypes derived from these genotypes and haplotypes.

In a preferred embodiment of the method, the trait of interest is a clinical response exhibited by a patient to some therapeutic treatment, for example, response to a drug targeting AGTR1 or response to a therapeutic treatment for a medical condition. As used herein, "medical condition" includes but is not limited to any condition or disease manifested as one or more physical and/or psychological symptoms for which treatment is desirable, and includes previously and newly identified diseases and other disorders. As used herein the term "clinical response" means any or all of the following: a quantitative measure of the response, no response, and adverse response (i.e., side effects).

In order to deduce a correlation between clinical response to a treatment and an AGTR1 genotype, haplotype, or haplotype pair, it is necessary to obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials. As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that the individuals included in the clinical population have been graded for the existence of the medical condition of interest. This is important in cases where the symptom(s) being presented by the patients can be caused by more than one underlying condition, and where treatment of the underlying conditions are not the same. An example of this would be where patients experience breathing difficulties that are due to either asthma or respiratory infections. If both sets were treated with an asthma medication, there would be a spurious group of apparent non-responders that did not actually have asthma. These people would affect the ability to detect any correlation between haplotype and treatment outcome. This grading of potential patients could employ a standard physical exam or one or more lab tests. Alternatively, grading of patients could use haplotyping for situations where there is a strong correlation between haplotype pair and disease susceptibility or severity.

The therapeutic treatment of interest is administered to each individual in the trial population and each individual's response to the treatment is measured using one or more predetermined criteria. It is contemplated that in many cases, the trial population will exhibit a range of responses and that the investigator will choose the number of responder groups (e.g., low, medium, high) made up by the various responses. In addition, the AGTR1 gene for each individual in the trial population is genotyped and/or haplotyped, which may be done before or after administering the treatment.

After both the clinical and polymorphism data have been obtained, correlations between individual response and AGTR1 genotype or haplotype content are created. Correlations may be produced in several ways. In one method, individuals are grouped by their AGTR1 genotype or haplotype (or haplotype pair) (also referred to as a polymorphism group), and then the averages and standard deviations of clinical responses exhibited by the members of each polymorphism group are calculated.

These results are then analyzed to determine if any observed variation in clinical response between polymorphism groups is statistically significant. Statistical analysis methods which may be used are described in L. D. Fisher and G. vanBelle, "Biostatistics: A Methodology for the Health Sciences", Wiley-Interscience (New York) 1993. This analysis may also include a regression calculation of which polymorphic sites in the AGTR1 gene give the most significant contribution to the differences in phenotype. One regression model useful in the invention is described in PCT Application Serial No. PCT/US00/17540, entitled "Methods for Obtaining and Using Haplotype Data".

A second method for finding correlations between AGTR1 haplotype content and clinical responses uses predictive models based on error-minimizing optimization algorithms. One of many possible optimization algorithms is a genetic algorithm (R. Judson, "Genetic Algorithms and Their Uses in Chemistry" in Reviews in Computational Chemistry, Vol. 10, pp. 1–73, K. B. Lipkowitz and D. B. Boyd, eds. (VCH Publishers, New York, 1997). Simulated annealing (Press et al., "Numerical Recipes in C: The Art of Scientific Computing", Cambridge University Press (Cambridge) 1992, Ch. 10), neural networks (E. Rich and K. Knight, "Artificial Intelligence", $2^{nd}$ Edition (McGraw-Hill, New York, 1991, Ch. 18), standard gradient descent methods (Press et al., supra, Ch. 10), or other global or local optimization approaches (see discussion in Judson, supra) could also be used. Preferably, the correlation is found using a genetic algorithm approach as described in PCT Application Serial No. PCT/US00/17540.

Correlations may also be analyzed using analysis of variation (ANOVA) techniques to determine how much of the variation in the clinical data is explained by different subsets of the polymorphic sites in the AGTR1 gene. As described in PCT Application Serial No. PCT/US00/17540, ANOVA is used to test hypotheses about whether a response variable is caused by or correlated with one or more traits or variables that can be measured (Fisher and vanBelle, supra, Ch. 10).

From the analyses described above, a mathematical model may be readily constructed by the skilled artisan that predicts clinical response as a function of AGTR1 genotype or haplotype content. Preferably, the model is validated in one or more follow-up clinical trials designed to test the model.

The identification of an association between a clinical response and a genotype or haplotype (or haplotype pair) for the AGTR1 gene may be the basis for designing a diagnostic method to determine those individuals who will or will not respond to the treatment, or alternatively, will respond at a lower level and thus may require more treatment, i.e., a greater dose of a drug. The diagnostic method may take one of several forms: for example, a direct DNA test (i.e., genotyping or haplotyping one or more of the polymorphic sites in the AGTR1 gene), a serological test, or a physical exam measurement. The only requirement is that there be a good correlation between the diagnostic test results and the underlying AGTR1 genotype or haplotype that is in turn correlated with the clinical response. In a preferred embodiment, this diagnostic method uses the predictive haplotyping method described above.

In another embodiment, the invention provides an isolated polynucleotide comprising a polymorphic variant of the AGTR1 gene or a fragment of the gene which contains at least one of the novel polymorphic sites described herein. The nucleotide sequence of a variant AGTR1 gene is identical to the reference genomic sequence for those portions of the gene examined, as described in the Examples below, except that it comprises a different nucleotide at one or more of the novel polymorphic sites PS1, PS2, PS4, and PS5, and may also comprise one or more additional polymorphisms selected from the group consisting of cytosine at PS3, guanine at PS6, and guanine at PS7. Similarly, the nucleotide sequence of a variant fragment of the AGTR1 gene is identical to the corresponding portion of the reference sequence except for having a different nucleotide at one or more of the novel polymorphic sites described herein. Thus, the invention specifically does not include polynucleotides comprising a nucleotide sequence identical to the reference sequence of the AGTR1 gene, which is defined by haplotype 9, (or other reported AGTR1 sequences) or to portions of the reference sequence (or other reported AGTR1 sequences), except for genotyping oligonucleotides as described above.

In a preferred embodiment, the polymorphic variant comprises a naturally-occurring isogene of the AGTR1 gene which is defined by any one of haplotypes 1–8 and 10 shown in Table 5 below. Thus, the sequence of the AGTR1 isogene of the invention comprises each of the regions of the reference genomic sequence examined, with the qualification that the nucleotide present at each of PS1–7 in that reference sequence is the allele shown in the corresponding haplotype.

The location of a polymorphism in a variant gene or fragment is identified by aligning its sequence against SEQ ID NO:1. The polymorphism is selected from the group consisting of adenine at PS1, thymine at PS2, cytosine at PS4, and thymine at PS5.

Polymorphic variants of the invention may be prepared by isolating a clone containing the AGTR1 gene from a human genomic library. The clone may be sequenced to determine the identity of the nucleotides at the novel polymorphic sites described herein. Any particular variant claimed herein could be prepared from this clone by performing in vitro mutagenesis using procedures well-known in the art.

AGTR1 isogenes may be isolated using any method that allows separation of the two "copies" of the AGTR1 gene present in an individual, which, as readily understood by the skilled artisan, may be the same allele or different alleles. Separation methods include targeted in vivo cloning (TWVC) in yeast as described in WO 98/01573, U.S. Pat. No. 5,866,404, and U.S. Pat. No. 5,972,614. Another method, which is described in U.S. Pat. No. 5,972,614, uses an allele specific oligonucleotide in combination with primer extension and exonuclease degradation to generate hemizygous DNA targets. Yet other methods are single molecule dilution (SMD) as described in Ruaño et al., Proc. Natl. Acad. Sci. 87:6296–6300, 1990; and allele specific PCR (Ruaño et al., 1989, supra; Ruaño et al., 1991, supra; Michalatos-Beloin et al., supra).

The invention also provides AGTR1 genome anthologies, which are collections of AGTR1 isogenes found in a given population. The population may be any group of at least two individuals, including but not limited to a reference population, a population group, a family population, a clinical population, and a same sex population. An AGTR1 genome anthology may comprise individual AGTR1 isogenes stored in separate containers such as microtest tubes, separate wells of a microtitre plate and the like. Alternatively, two or more groups of the AGTR1 isogenes in the anthology may be stored in separate containers. Individual isogenes or groups of isogenes in a genome anthology may be stored in any convenient and stable form, including but not limited to in buffered solutions, as DNA precipitates, freeze-dried preparations and the like. A preferred AGTR1 genome anthology of the invention comprises a set of isogenes defined by the haplotypes shown in Table 5 below.

An isolated polynucleotide containing a polymorphic variant nucleotide sequence of the invention may be operably linked to one or more expression regulatory elements in a recombinant expression vector capable of being propagated and expressing the encoded AGTR1 protein in a prokaryotic or a eukaryotic host cell. Examples of expression regulatory elements which may be used include, but are not limited to, the lac system, operator and promoter regions of phage lambda, yeast promoters, and promoters derived from vaccinia virus, adenovirus, retroviruses, or SV40. Other regulatory elements include, but are not limited to, appropriate leader sequences, termination codons, polyadenylation signals, and other sequences required for the appropriate transcription and subsequent translation of the nucleic acid sequence in a given host cell. Of course, the correct combinations of expression regulatory elements will depend on the host system used. In addition, it is understood that the expression vector contains any additional elements necessary for its transfer to and subsequent replication in the host cell. Examples of such elements include, but are not limited to, origins of replication and selectable markers. Such expression vectors are commercially available or are readily constructed using methods known to those in the art (e.g., F. Ausubel et al., 1987, in "Current Protocols in Molecular Biology", John Wiley and Sons, New York, N.Y.). Host cells which may be used to express the variant AGTR1 sequences of the invention include, but are not limited to, eukaryotic and mammalian cells, such as animal, plant, insect and yeast cells, and prokaryotic cells, such as E. coli, or algal cells as known in the art. The recombinant expression vector may be introduced into the host cell using any method known to those in the art including, but not limited to, microinjection, electroporation, particle bombardment, transduction, and transfection using DEAE-dextran, lipofection, or calcium phosphate (see e.g., Sambrook et al. (1989) in "Molecular Cloning. A Laboratory Manual", Cold Spring Harbor Press, Plainview, N.Y.). In a preferred aspect, eukaryotic expression vectors that function in eukaryotic cells, and preferably mammalian cells, are used. Non-limiting examples of such vectors include vaccinia virus vectors, adenovirus vectors, herpes virus vectors, and baculovirus transfer vectors. Preferred eukaryotic cell lines include COS cells, CHO cells, HeLa cells, NIH/3T3 cells, and embryonic stem cells (Thomson, J. A. et al., 1998 Science 282:1145–1147). Particularly preferred host cells are mammalian cells.

As will be readily recognized by the skilled artisan, expression of polymorphic variants of the AGTR1 gene will produce AGTR1 mRNAs varying from each other at any polymorphic site retained in the spliced and processed mRNA molecules. These mRNAs can be used for the preparation of an AGTR1 cDNA comprising a nucleotide sequence which is a polymorphic variant of the AGTR1 reference coding sequence shown in FIG. 2. Thus, the invention also provides AGTR1 mRNAs and corresponding cDNAs which comprise a nucleotide sequence that is identical to SEQ ID NO:2 (FIG. 2), or its corresponding RNA sequence, except for having one or more polymorphisms selected from the group consisting of cytosine at a position corresponding to nucleotide 611 and thymine at a position corresponding to nucleotide 1007, and may also comprise one or more additional polymorphisms selected from the group consisting of cytosine at a position corresponding to nucleotide 573 and guanine at a position corresponding to nucleotide 1062. A particularly preferred polymorphic cDNA variant comprises the coding sequence of an AGTR1 isogene defined by haplotypes 1–8 and 10. Fragments of these variant mRNAs and cDNAs are included in the scope of the invention, provided they contain the novel polymorphisms described herein. The invention specifically excludes polynucleotides identical to previously identified and characterized AGTR1 cDNAs and fragments thereof. Polynucleotides comprising a variant RNA or DNA sequence may be isolated from a biological sample using well-known molecular biological procedures or may be chemically synthesized.

As used herein, a polymorphic variant of an AGTR1 gene fragment comprises at least one novel polymorphism identified herein and has a length of at least 10 nucleotides and may range up to the full length of the gene. Preferably, such fragments are between 100 and 3000 nucleotides in length, and more preferably between 200 and 2000 nucleotides in length, and most preferably between 500 and 1000 nucleotides in length.

In describing the AGTR1 polymorphic sites identified herein, reference is made to the sense strand of the gene for convenience. However, as recognized by the skilled artisan, nucleic acid molecules containing the AGTR1 gene may be complementary double stranded molecules and thus reference to a particular site on the sense strand refers as well to the corresponding site on the complementary antisense strand. Thus, reference may be made to the same polymorphic site on either strand and an oligonucleotide may be designed to hybridize specifically to either strand at a target region containing the polymorphic site. Thus, the invention also includes single-stranded polynucleotides which are complementary to the sense strand of the AGTR1 genomic variants described herein.

Polynucleotides comprising a polymorphic gene variant or fragment may be useful for therapeutic purposes. For example, where a patient could benefit from expression, or increased expression, of a particular AGTR1 protein isoform, an expression vector encoding the isoform may be administered to the patient. The patient may be one who lacks the AGTR1 isogene encoding that isoform or may already have at least one copy of that isogene.

In other situations, it may be desirable to decrease or block expression of a particular AGTR1 isogene. Expression of an AGTR1 isogene may be turned off by transforming a targeted organ, tissue or cell population with an expression vector that expresses high levels of untranslatable mRNA for the isogene. Alternatively, oligonucleotides directed against the regulatory regions (e.g., promoter, introns, enhancers, 3' untranslated region) of the isogene may block transcription. Oligonucleotides targeting the transcription initiation site, e.g., between positions −10 and +10 from the start site are preferred. Similarly, inhibition of transcription can be achieved using oligonucleotides that base-pair with region (s) of the isogene DNA to form triplex DNA (see e.g., Gee et al. in Huber, B. E. and B. I. Carr, Molecular and Immunologic Approaches, Futura Publishing Co., Mt. Kisco, N.Y., 1994). Antisense oligonucleotides may also be designed to block translation of AGTR1 mRNA transcribed from a particular isogene. It is also contemplated that ribozymes may be designed that can catalyze the specific cleavage of AGTR1 mRNA transcribed from a particular isogene.

The oligonucleotides may be delivered to a target cell or tissue by expression from a vector introduced into the cell or tissue in vivo or ex vivo. Alternatively, the oligonucleotides may be formulated as a pharmaceutical composition for administration to the patient. Oligoribonucleotides and/or oligodeoxynucleotides intended for use as antisense oligonucleotides may be modified to increase stability and half-life. Possible modifications include, but are not limited to phosphorothioate or 2' O-methyl linkages, and the inclusion of nontraditional bases such as inosine and queosine, as well as acetyl-, methyl-, thio-, and similarly modified forms of adenine, cytosine, guanine, thymine, and uracil which are not as easily recognized by endogenous nucleases.

The invention also provides an isolated polypeptide comprising a polymorphic variant of the reference AGTR1 amino acid sequence shown in FIG. 3. The location of a variant amino acid in an AGTR1 polypeptide or fragment of the invention is identified by aligning its sequence against SEQ ID NO:3 (FIG. 3). An AGTR1 protein variant of the invention comprises an amino acid sequence identical to SEQ ID NO:3 except for having one or more variant amino acids selected from the group consisting of serine at a position corresponding to amino acid position 204 and methionine at a position corresponding to amino acid position 336. The invention specifically excludes amino acid sequences identical to those previously identified for AGTR1, including SEQ ID NO:3, and previously described fragments thereof. AGTR1 protein variants included within the invention comprise all amino acid sequences based on SEQ ID NO:3 and having the combination of amino acid variations described in Table 2 below. In preferred embodiments, an AGTR1 protein variant of the invention is encoded by an isogene defined by one of the observed haplotypes shown in Table 5.

TABLE 2

Novel Polymorphic Variants of AGTR1
Polymorphic Amino Acid Position and Identities

| Variant Number | 204 | 336 |
| --- | --- | --- |
| 1 | F | M |
| 2 | S | T |
| 3 | S | M |

The invention also includes AGTR1 peptide variants, which are any fragments of an AGTR1 protein variant that contain one or more of the amino acid variations shown in Table 2 An AGTR1 peptide variant is at least 6 amino acids in length and is preferably any number between 6 and 30 amino acids long, more preferably between 10 and 25, and most preferably between 15 and 20 amino acids long. Such AGTR1 peptide variants may be useful as antigens to generate antibodies specific for one of the above AGTR1 isoforms. In addition, the AGTR1 peptide variants may be useful in drug screening assays.

An AGTR1 variant protein or peptide of the invention may be prepared by chemical synthesis or by expressing one of the variant AGTR1 genomic and cDNA sequences as described above. Alternatively, the AGTR1 protein variant may be isolated from a biological sample of an individual having an AGTR1 isogene which encodes the variant protein. Where the sample contains two different AGTR1 isoforms (i.e., the individual has different AGTR1 isogenes), a particular AGTR1 isoform of the invention can be isolated by immunoaffinity chromatography using an antibody which specifically binds to that particular AGTR1 isoform but does not bind to the other AGTR1 isoform.

The expressed or isolated AGTR1 protein may be detected by methods known in the art, including Coomassie blue staining, silver staining, and Western blot analysis using antibodies specific for the isoform of the AGTR1 protein as discussed further below. AGTR1 variant proteins can be purified by standard protein purification procedures known in the art, including differential precipitation, molecular sieve chromatography, ion-exchange chromatography, isoelectric focusing, gel electrophoresis, affinity and immunoaffinity chromatography and the like. (Ausubel et. al., 1987, In Current Protocols in Molecular Biology John Wiley and Sons, New York, N.Y.). In the case of immunoaffinity chromatography, antibodies specific for a particular polymorphic variant may be used.

A polymorphic variant AGTR1 gene of the invention may also be fused in frame with a heterologous sequence to encode a chimeric AGTR1 protein. The non-AGTR1 portion of the chimeric protein may be recognized by a commercially available antibody. In addition, the chimeric protein may also be engineered to contain a cleavage site located between the AGTR1 and non-AGTR1 portions so that the AGTR1 protein may be cleaved and purified away from the non-AGTR1 portion.

An additional embodiment of the invention relates to using a novel AGTR1 protein isoform in any of a variety of drug screening assays. Such screening assays may be performed to identify agents that bind specifically to all known AGTR1 protein isoforms or to only a subset of one or more of these isoforms. The agents may be from chemical compound libraries, peptide libraries and the like. The AGTR1 protein or peptide variant may be free in solution or affixed to a solid support. In one embodiment, high throughput screening of compounds for binding to an AGTR1 variant may be accomplished using the method described in PCT application WO84/03565, in which large numbers of test compounds are synthesized on a solid substrate, such as plastic pins or some other surface, contacted with the AGTR1 protein(s) of interest and then washed. Bound AGTR1 protein(s) are then detected using methods well-known in the art.

In another embodiment, a novel AGTR1 protein isoform may be used in assays to measure the binding affinities of one or more candidate drugs targeting the AGTR1 protein.

In yet another embodiment, when a particular AGTR1 haplotype or group of AGTR1 haplotypes encodes an AGTR1 protein variant with an amino acid sequence distinct from that of AGTR1 protein isoforms encoded by other AGTR1 haplotypes, then detection of that particular AGTR1 haplotype or group of AGTR1 haplotypes may be accomplished by detecting expression of the encoded AGTR1 protein variant using any of the methods described herein or otherwise commonly known to the skilled artisan.

In another embodiment, the invention provides antibodies specific for and immunoreactive with one or more of the novel AGTR1 variant proteins described herein. The antibodies may be either monoclonal or polyclonal in origin. The AGTR1 protein or peptide variant used to generate the antibodies may be from natural or recombinant sources or produced by chemical synthesis using synthesis techniques known in the art. If the AGTR1 protein variant is of insufficient size to be antigenic, it may be conjugated, complexed, or otherwise covalently linked to a carrier molecule to enhance the antigenicity of the peptide. Examples of carrier molecules, include, but are not limited to, albumins (e.g., human, bovine, fish, ovine), and keyhole limpet hemocyanin (Basic and Clinical Immunology, 1991, Eds. D. P. Stites, and A. I. Terr, Appleton and Lange, Norwalk Conn., San Mateo, Calif.).

In one embodiment, an antibody specifically immunoreactive with one of the novel protein isoforms described herein is administered to an individual to neutralize activity of the AGTR1 isoform expressed by that individual. The antibody may be formulated as a pharmaceutical composition which includes a pharmaceutically acceptable carrier.

Antibodies specific for and immunoreactive with one of the novel protein isoforms described herein may be used to immunoprecipitate the AGTR1 protein variant from solution as well as react with AGTR1 protein isoforms on Western or immunoblots of polyacrylamide gels on membrane supports or substrates. In another preferred embodiment, the antibodies will detect AGTR1 protein isoforms in paraffin or frozen tissue sections, or in cells which have been fixed or unfixed and prepared on slides, coverslips, or the like, for use in immunocytochemical, immunohistochemical, and immunofluorescence techniques.

In another embodiment, an antibody specifically immunoreactive with one of the novel AGTR1 protein variants described herein is used in immunoassays to detect this variant in biological samples. In this method, an antibody of the present invention is contacted with a biological sample and the formation of a complex between the AGTR1 protein variant and the antibody is detected. As described, suitable immunoassays include radioimmunoassay, Western blot assay, immunofluorescent assay, enzyme linked immunoassay (ELISA), chemiluminescent assay, immunohistochemical assay, immunocytochemical assay, and the like (see, e.g., Principles and Practice of Immunoassay, 1991, Eds. Christopher P. Price and David J. Neoman, Stockton Press, New York, N.Y.; Current Protocols in Molecular Biology, 1987, Eds. Ausubel et al., John Wiley and Sons, New York, N.Y.). Standard techniques known in the art for ELISA are described in Methods in Immunodiagnosis, 2nd Ed., Eds. Rose and Bigazzi, John Wiley and Sons, New York 1980; and Campbell et al., 1984, Methods in Immunology, W. A. Benjamin, Inc.). Such assays may be direct, indirect, competitive, or noncompetitive as described in the art (see, e.g., Principles and Practice of Immunoassay, 1991, Eds. Christopher P. Price and David J. Neoman, Stockton Pres, N.Y., N.Y.; and Oellirich, M., 1984, J. Clin. Chem. Clin. Biochem., 22:895–904). Proteins may be isolated from test specimens and biological samples by conventional methods, as described in Current Protocols in Molecular Biology, supra.

Exemplary antibody molecules for use in the detection and therapy methods of the present invention are intact immunoglobulin molecules, substantially intact immunoglobulin molecules, or those portions of immunoglobulin molecules that contain the antigen binding site. Polyclonal or monoclonal antibodies may be produced by methods conventionally known in the art (e.g., Kohler and Milstein, 1975, Nature, 256:495–497; Campbell Monoclonal Antibody Technology, the Production and Characterization of Rodent and Human Hybridomas, 1985, In: Laboratory Techniques in Biochemistry and Molecular Biology, Eds. Burdon et al., Volume 13, Elsevier Science Publishers, Amsterdam). The antibodies or antigen binding fragments thereof may also be produced by genetic engineering. The technology for expression of both heavy and light chain genes in E. coli is the subject of PCT patent applications, publication number WO 901443, WO 901443 and WO 9014424 and in Huse et al., 1989, Science, 246:1275–1281. The antibodies may also be humanized (e.g., Queen, C. et al. 1989 Proc. Natl. Acad. Sci.USA 86; 10029).

Effect(s) of the polymorphisms identified herein on expression of AGTR1 may be investigated by preparing recombinant cells and/or nonhuman recombinant organisms, preferably recombinant animals, containing a polymorphic variant of the AGTR1 gene. As used herein, "expression" includes but is not limited to one or more of the following: transcription of the gene into precursor mRNA; splicing and other processing of the precursor mRNA to produce mature mRNA; mRNA stability; translation of the mature mRNA into AGTR1 protein (including codon usage and tRNA availability); and glycosylation and/or other modifications of the translation product, if required for proper expression and function.

To prepare a recombinant cell of the invention, the desired AGTR1 isogene may be introduced into the cell in a vector such that the isogene remains extrachromosomal. In such a situation, the gene will be expressed by the cell from the extrachromosomal location. In a preferred embodiment, the AGTR1 isogene is introduced in a cell in such a way that it recombines with the endogenous AGTR1 gene present in the cell. Such recombination requires the occurrence of a double recombination event, thereby resulting in the desired AGTR1 gene polymorphism. Vectors for the introduction of genes both for recombination and for extrachromosomal maintenance are known in the art, and any suitable vector or vector construct may be used in the invention. Methods such as electroporation, particle bombardment, calcium phosphate co-precipitation and viral transduction for introducing DNA into cells are known in the art; therefore, the choice of method may lie with the competence and preference of the skilled practitioner. Examples of cells into which the AGTR1 isogene may be introduced include, but are not limited to, continuous culture cells, such as COS, NIH/3T3, and primary or culture cells of the relevant tissue type, i.e., they express the AGTR1 isogene. Such recombinant cells can be used to compare the biological activities of the different protein variants.

Recombinant nonhuman organisms, i.e., transgenic animals, expressing a variant AGTR1 gene are prepared using standard procedures known in the art. Preferably, a construct comprising the variant gene is introduced into a nonhuman animal or an ancestor of the animal at an embryonic stage, i.e., the one-cell stage, or generally not later than about the eight-cell stage. Transgenic animals carrying the constructs of the invention can be made by several methods known to those having skill in the art. One method involves transfecting into the embryo a retrovirus constructed to contain one or more insulator elements, a gene or genes of interest, and other components known to those skilled in the art to provide a complete shuttle vector harboring the insulated gene(s) as a transgene, see e.g., U.S. Pat. No. 5,610,053. Another method involves directly injecting a transgene into the embryo. A third method involves the use of embryonic stem cells. Examples of animals into which the AGTR1 isogenes may be introduced include, but are not limited to, mice, rats, other rodents, and nonhuman primates (see "The Introduction of Foreign Genes into Mice" and the cited references therein, In: Recombinant DNA, Eds. J. D. Watson, M. Gilman, J. Witkowski, and M. Zoller; W. H. Freeman and Company, New York, pages 254–272). Transgenic animals stably expressing a human AGTR1 isogene and producing human AGTR1 protein can be used as biological models for studying diseases related to abnormal AGTR1 expression and/or activity, and for screening and assaying various candidate drugs, compounds, and treatment regimens to reduce the symptoms or effects of these diseases.

An additional embodiment of the invention relates to pharmaceutical compositions for treating disorders affected by expression or function of a novel AGTR1 isogene described herein. The pharmaceutical composition may comprise any of the following active ingredients: a polynucleotide comprising one of these novel AGTR1 isogenes; an antisense oligonucleotide directed against one of the novel AGTR1 isogenes, a polynucleotide encoding such an antisense oligonucleotide, or another compound which inhibits expression of a novel AGTR1 isogene described herein. Preferably, the composition contains the active ingredient in a therapeutically effective amount. By therapeutically effective amount is meant that one or more of the symptoms relating to disorders affected by expression or function of a novel AGTR1 isogene is reduced and/or eliminated. The composition also comprises a pharmaceutically acceptable carrier, examples of which include, but are not limited to, saline, buffered saline, dextrose, and water. Those skilled in the art may employ a formulation most suitable for the active ingredient, whether it is a polynucleotide, oligonucleotide, protein, peptide or small molecule antagonist. The pharmaceutical composition may be administered alone or in combination with at least one other agent, such as a stabilizing compound. Administration of the pharmaceutical composition may be by any number of routes including, but not limited to oral, intravenous, intramuscular, intra-arterial, intramedullary, intrathecal, intraventricular, intradermal, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.).

For any composition, determination of the therapeutically effective dose of active ingredient and/or the appropriate route of administration is well within the capability of those skilled in the art. For example, the dose can be estimated initially either in cell culture assays or in animal models. The animal model may also be used to determine the appropriate concentration range and route of administration. Such information can then be used to determine useful doses and routes for administration in humans. The exact dosage will be determined by the practitioner, in light of factors relating to the patient requiring treatment, including but not limited to severity of the disease state, general health, age, weight and gender of the patient, diet, time and frequency of administration, other drugs being taken by the patient, and tolerance/response to the treatment.

Any or all analytical and mathematical operations involved in practicing the methods of the present invention may be implemented by a computer. In addition, the computer may execute a program that generates views (or screens) displayed on a display device and with which the user can interact to view and analyze large amounts of information relating to the AGTR1 gene and its genomic variation, including chromosome location, gene structure, and gene family, gene expression data, polymorphism data, genetic sequence data, and clinical data population data (e.g., data on ethnogeographic origin, clinical responses, genotypes, and haplotypes for one or more populations). The AGTR1 polymorphism data described herein may be stored as part of a relational database (e.g., an instance of an Oracle database or a set of ASCII flat files). These polymorphism data may be stored on the computer's hard drive or may, for example, be stored on a CD-ROM or on one or more other storage devices accessible by the computer. For example, the data may be stored on one or more databases in communication with the computer via a network.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

The Examples herein are meant to exemplify the various aspects of carrying out the invention and are not intended to limit the scope of the invention in any way. The Examples do not include detailed descriptions for conventional methods employed, such as in the performance of genomic DNA isolation, PCR and sequencing procedures. Such methods are well-known to those skilled in the art and are described in numerous publications, for example, Sambrook, Fritsch, and Maniatis, "Molecular Cloning: A Laboratory Manual", $2^{nd}$ Edition, Cold Spring Harbor Laboratory Press, USA, (1989).

Example 1

This example illustrates examination of various regions of the AGTR1 gene for polymorphic sites.

Amplification of Target Regions

The following target regions were amplified using either the PCR primers represented below or 'tailed' PCR primers, each of which includes a universal sequence forming a noncomplementary 'tail' attached to the 5' end of each unique sequence in the PCR primer pairs. The universal 'tail' sequence for the forward PCR primers comprises the sequence 5'-TGTAAAACGACGGCCAGT-3' (SEQ ID NO:24) and the universal 'tail' sequence for the reverse PCR primers comprises the sequence 5'-AGGAAACAGCTATGACCAT-3' (SEQ ID NO:25). The nucleotide positions of the first and last nucleotide of the forward and reverse primers for each region amplified are presented below and correspond to positions in FIG. 1.

| | PCR Primer Pairs | | |
|---|---|---|---|
| Fragment No. | Forward Primer | Reverse Primer | PCR Product |
| Fragment 1 | 11–30 | complement of 622–603 | 612 nt |
| Fragment 2 | 255–274 | complement of 872–850 | 618 nt |
| Fragment 3 | 504–525 | complement of 1312–1292 | 809 nt |
| Fragment 4 | 884–907 | complement of 1498–1476 | 615 nt |
| Fragment 5 | 1016–1038 | complement of 1743–1721 | 728 nt |

These primer pairs were used in PCR reactions containing genomic DNA isolated from immortalized cell lines for each member of the Index Repository. The PCR reactions were carried out under the following conditions:

| | |
|---|---|
| Reaction volume = | 10 µl |
| 10 × Advantage 2 Polymerase reaction buffer (Clontech) = | 1 µl |
| 100 ng of human genomic DNA = | 1 µl |
| 10 mM dNTP = | 0.4 µl |
| Advantage 2 Polymerase enzyme mix (Clontech) = | 0.2 µl |
| Forward Primer (10 µM) = | 0.4 µl |
| Reverse Primer (10 µM) = | 0.4 µl |
| Water = | 6.6 µl |

Amplification profile:

97° C. - 2 min.   1 cycle
97° C. - 15 sec.  ⎫
70° C. - 45 sec.  ⎬ 10 cycles
72° C. - 45 sec.  ⎭
97° C. - 15 sec.  ⎫
64° C. - 45 sec.  ⎬ 35 cycles
72° C. - 45 sec.  ⎭

Sequencing of PCR Products

The PCR products were purified using a Whatman/Polyfiltronics 100 µl 384 well unifilter plate essentially according to the manufacturers protocol. The purified DNA was eluted in 50 µl of distilled water. Sequencing reactions were set up using Applied Biosystems Big Dye Terminator chemistry essentially according to the manufacturers protocol. The purified PCR products were sequenced in both directions using either the primer sets represented below with the positions of their first and last nucleotide corresponding to positions in FIG. 1, or the appropriate universal 'tail' sequence as a primer. Reaction products were purified by isopropanol precipitation, and run on an Applied Biosystems 3700 DNA Analyzer.

| Sequencing Primer Pairs | | |
|---|---|---|
| Fragment No. | Forward Primer | Reverse Primer |
| Fragment 1 | 20–41 | complement of 464–445 |
| Fragment 2 | Tailed Seq. | |
| Fragment 3 | 594–614 | complement of 1137–1118 |
| Fragment 4 | 908–927 | complement of 1447–1427 |
| Fragment 5 | 1117–1136 | complement of 1681–1661 |

Analysis of Sequences for Polymorphic Sites

Sequence information for a minimum of 80 humans was analyzed for the presence of polymorphisms using the Polyphred program (Nickerson et al., *Nucleic Acids Res.* 14:2745–2751, 1997). The presence of a polymorphism was confirmed on both strands. The polymorphisms and their locations in the AGTR1 gene are listed in Table 3 below.

TABLE 3

Polymorphic Sites Identified in the AGTR1 Gene

| Polymorphic Site Number | PolyId[a] | Nucleotide Position | Reference Allele | Variant Allele | CDS Variant Position | AA Variant |
|---|---|---|---|---|---|---|
| PS1 | 2506614 | 104 | T | A | | |
| PS2 | 2506616 | 348 | G | T | | |
| PS3[R] | 2506620 | 1036 | T | C | 573 | L191L |
| PS4 | 2506622 | 1074 | T | C | 611 | F204S |
| PS5 | 2506626 | 1470 | C | T | 1007 | T336M |
| PS6[R] | 2506628 | 1525 | A | G | 1062 | P354P |
| PS7[R] | 2506630 | 1613 | T | G | | |

[a]PolyId is a unique identifier assigned to each PS by Genaissance Pharmaceuticals, Inc.
[R]Previously reported in the literature

Example 2

This example illustrates analysis of the AGTR1 polymorphisms identified in the Index Repository for human genotypes and haplotypes.

The different genotypes containing these polymorphisms that were observed in the reference population are shown in Table 4 below, with the haplotype pair indicating the combination of hapotypes determined for the individual using the haplotype derivation protocol described below. In Table 4, homozygous positions are indicated by one nucleotide and heterozygous positions are indicated by two nucleotides. Missing nucleotides in any given genotype in Table 4 were inferred based on linkage disequilibrium and/or Mendelian inheritance.

TABLE 4

Genotypes and Haplotype Pairs Observed for AGTR1 Gene

| Geno-type Number | Polymorphic Sites | | | | | | | HAP | Pair |
|---|---|---|---|---|---|---|---|---|---|
| | PS1 | PS2 | PS3 | PS4 | PS5 | P56 | PS7 | | |
| 1 | T | G | T | T | C | A | T | 9 | 9 |
| 2 | T | G | C | T | C | A | T | 5 | 5 |
| 3 | A | G | C | T | C | G | T | 3 | 3 |
| 4 | A | G | C | T | C | A | T | 1 | 1 |
| 5 | T/A | G | C | T | C | A/G | T/G | 5 | 2 |
| 6 | A/T | G | C | T | C | G | T | 3 | 6 |
| 7 | T/A | G | C | T | C | A | T | 5 | 1 |
| 8 | T | G | T | T/C | C | A | T | 9 | 8 |
| 9 | T | G | C | T | C | A/G | T | 5 | 6 |
| 10 | T/A | G | C | T | C | A/G | T | 5 | 3 |
| 11 | T/A | G | T/C | T | C | A | T | 9 | 1 |
| 12 | T | G/T | C/T | T | C | A | T | 5 | 10 |
| 13 | T | G | T/C | T | C/T | A | T | 9 | 7 |
| 14 | T | G/T | T | T | C | A | T | 9 | 10 |
| 15 | T | G | T/C | T | C | A | T | 9 | 5 |
| 16 | T | G | C | T | C | A | T/G | 5 | 4 |

The haplotype pairs shown in Table 4 were estimated from the unphased genotypes using a computer-implemented extension of Clark's algorithm (Clark, A. G. 1990 Mol Bio Evol 7, 111–122) for assigning haplotypes to unrelated individuals in a population sample, as described in U.S. Provisional Application Serial No. 60/198,340 entitled "A Method and System for Determining Haplotypes from a Collection of Polymorphisms" and the corresponding International Application filed Apr. 18, 2001. In this method, haplotypes are assigned directly from individuals who are homozygous at all sites or heterozygous at no more than one of the variable sites. This list of haplotypes is augmented with haplotypes obtained from two families (one three-generation Caucasian family and one two-generation African-American family) and then used to deconvolute the unphased genotypes in the remaining (multiply heterozygous) individuals.

By following this protocol, it was determined that the Index Repository examined herein and, by extension, the general population contains the 10 human AGTR1 haplotypes shown in Table 5 below.

An AGTR1 isogene defined by a full-haplotype shown in Table 5 below comprises the regions of the SEQ ID NOS indicated in Table 5, with their corresponding set of polymorphic locations and identities, which are also set forth in Table 5.

TABLE 5

Haplotypes Identified in the AGTR1 Gene

| Haplotype Number[a] | | | | | | | | | | PS Number[b] | Nt Position[c] | SEQ ID NO[d] | Region Examined[e] |
| 1 | 2 | 3 | 4 | 5 | 6 | 7 | 8 | 9 | 10 | | | | |
|---|---|---|---|---|---|---|---|---|---|---|---|---|---|
| A | A | A | T | T | T | T | T | T | T | 1 | 104/30 | 26/27 | 11-1743 |
| G | G | G | G | G | G | G | G | G | T | 2 | 348/150 | 26/27 | 11-1743 |
| C | C | C | C | C | C | C | T | T | T | 3 | 1036/270 | 26/27 | 11-1743 |
| T | T | T | T | T | T | T | C | T | T | 4 | 1074/390 | 26/27 | 11-1743 |
| C | C | C | C | C | C | T | C | C | C | 5 | 1470/510 | 26/27 | 11-1743 |
| A | G | G | A | A | G | A | A | A | A | 6 | 1525/630 | 26/27 | 11-1743 |
| T | G | T | G | T | T | T | T | T | T | 7 | 1613/750 | 26/27 | 11-1743 |

[a]Alleles for haplotypes are presented 5' to 3' in each column
[b]PS = polymorphic site;
[c]Position of PS within the indicated SEQ ID NO, with the 1st position number referring to the first SEQ ID NO and the 2nd position number referring to the 2nd SEQ ID NO;
[d]1st SEQ ID NO refers to FIG. 1, with the two alternative allelic variants of each polymorphic site indicated by the appropriate nucleotide symbol; 2nd SEQ ID NO is a modified version of the 1st SEQ ID NO that comprises the context sequence of each polymorphic site (PS) 1–7, to facilitate electronic searching of the haplotypes;
[e]Region examined represents the nucleotide positions defining the start and stop positions within the 1st SEQ ID NO of the sequenced region.

SEQ ID NO:26 refers to FIG. 1, with the two alternative allelic variants of each polymorphic site indicated by the appropriate nucleotide symbol. SEQ ID NO:27 is a modified version of SEQ ID NO:26 that shows the context sequence of each polymorphic site 1–7 in a uniform format to facilitate electronic searching of the AGTR1 haplotypes. For each polymorphic site, SEQ ID NO:27 contains a block of 60 bases of the nucleotide sequence encompassing the centrally-located polymorphic site at the 30$^{th}$ position, followed by 60 bases of unspecified sequence to represent that each PS is separated by genomic sequence whose composition is defined elsewhere herein.

Table 6 below shows the percent of chromosomes characterized by a given AGTR1 haplotype for all unrelated individuals in the Index Repository for which haplotype data was obtained. The percent of these unrelated individuals who have a given AGTR1 haplotype pair is shown in Table 7. In Tables 6 and 7, the "Total" column shows this frequency data for all of these unrelated individuals, while the other columns show the frequency data for these unrelated individuals categorized according to their self-identified ethnogeographic origin. Abbreviations used in Tables 6 and 7 are AF=African Descent, AS=Asian, CA=Caucasian, HL=Hispanic-Latino, and NA=Native American.

TABLE 6

Frequency of Observed AGTR1 Haplotypes In Unrelated Individuals

| HAP No. | HAP ID | Total | CA | AF | AS | HL | NA |
|---|---|---|---|---|---|---|---|
| 1 | 8047501 | 3.05 | 0.0 | 12.5 | 0.0 | 0.0 | 0.0 |
| 2 | 8047506 | 0.61 | 0.0 | 0.0 | 0.0 | 2.78 | 0.0 |
| 3 | 8047499 | 3.05 | 0.0 | 12.5 | 0.0 | 0.0 | 0.0 |
| 4 | 8047503 | 1.22 | 0.0 | 5.0 | 0.0 | 0.0 | 0.0 |
| 5 | 8047498 | 34.76 | 42.86 | 35.0 | 20.0 | 41.67 | 33.33 |
| 6 | 8047502 | 1.83 | 0.0 | 5.0 | 0.0 | 2.78 | 0.0 |
| 7 | 8047504 | 0.61 | 0.0 | 0.0 | 2.5 | 0.0 | 0.0 |
| 8 | 8047505 | 0.61 | 0.0 | 0.0 | 2.5 | 0.0 | 0.0 |
| 9 | 8047497 | 51.22 | 57.14 | 30.0 | 62.5 | 52.78 | 66.67 |
| 10 | 8047500 | 3.05 | 0.0 | 0.0 | 12.5 | 0.0 | 0.0 |

TABLE 7

Frequency of Observed AGTR1 Haplotype Pairs In Unrelated Individuals

| HAP1 | HAP2 | Total | CA | AF | AS | HL | NA |
|---|---|---|---|---|---|---|---|
| 9 | 9 | 25.61 | 23.81 | 15.0 | 40.0 | 22.22 | 33.33 |
| 5 | 5 | 7.32 | 9.52 | 5.0 | 10.0 | 5.56 | 0.0 |
| 3 | 3 | 1.22 | 0.0 | 5.0 | 0.0 | 0.0 | 0.0 |
| 1 | 1 | 1.22 | 0.0 | 5.0 | 0.0 | 0.0 | 0.0 |
| 5 | 2 | 1.22 | 0.0 | 0.0 | 0.0 | 5.56 | 0.0 |
| 3 | 6 | 1.22 | 0.0 | 5.0 | 0.0 | 0.0 | 0.0 |
| 5 | 1 | 2.44 | 0.0 | 10.0 | 0.0 | 0.0 | 0.0 |
| 9 | 8 | 1.22 | 0.0 | 0.0 | 5.0 | 0.0 | 0.0 |
| 5 | 6 | 2.44 | 0.0 | 5.0 | 0.0 | 5.56 | 0.0 |
| 5 | 3 | 2.44 | 0.0 | 10.0 | 0.0 | 0.0 | 0.0 |
| 9 | 1 | 1.22 | 0.0 | 5.0 | 0.0 | 0.0 | 0.0 |
| 5 | 10 | 1.22 | 0.0 | 0.0 | 5.0 | 0.0 | 0.0 |
| 9 | 7 | 1.22 | 0.0 | 0.0 | 5.0 | 0.0 | 0.0 |
| 9 | 10 | 4.88 | 0.0 | 0.0 | 20.0 | 0.0 | 0.0 |
| 9 | 5 | 42.68 | 66.67 | 25.0 | 15.0 | 61.11 | 66.67 |
| 5 | 4 | 2.44 | 0.0 | 10.0 | 0.0 | 0.0 | 0.0 |

The size and composition of the Index Repository were chosen to represent the genetic diversity across and within four major population groups comprising the general United States population. For example, as described in Table 1 above, this repository contains approximately equal sample sizes of African-descent, Asian-American, European-American, and Hispanic-Latino population groups. Almost all individuals representing each group had all four grandparents with the same ethnogeographic background. The number of unrelated individuals in the Index Repository provides a sample size that is sufficient to detect SNPs and haplotypes that occur in the general population with high statistical certainty. For instance, a haplotype that occurs with a frequency of 5% in the general population has a probability higher than 99.9% of being observed in a sample of 80 individuals from the general population. Similarly, a haplotype that occurs with a frequency of 10% in a specific population group has a 99% probability of being observed in a sample of 20 individuals from that population group. In addition, the size and composition of the Index Repository means that the relative frequencies determined therein for the haplotypes and haplotype pairs of the AGTR1 gene are likely to be similar to the relative frequencies of these AGTR1 haplotypes and haplotype pairs in the general U.S. population and in the four population groups represented in the Index Repository. The genetic diversity observed for the three Native Americans is presented because it is of scientific interest, but due to the small sample size it lacks statistical significance.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated in their entirety by reference. The discussion of references herein is intended merely to summarize the assertions made by their authors and no admission is made that any reference constitutes prior art. Applicants reserve the right to challenge the accuracy and pertinency of the cited references.

What is claimed is:

1. An isolated polynucleotide comprising a nucleotide sequence for an angiotensin receptor 1 (AGTR1) isogene, wherein the nucleotide sequence is selected from
   (a) a first nucleotide sequence comprising nucleotides 11–1743 of SEQ ID NO:26 and having adenine at position 104, guanine at position 348, cytosine at position 1036, thymine at position 1074, cytosine at position 1470, guanine at position 1525, and thymine at position 1613, and
   (b) a second nucleotide sequence which is complementary to the first nucleotide sequence.

2. A vector comprising the isolated polynucleotide of claim 1.

3. The vector of claim 2, which is selected from a vaccinia virus vector, a herpes virus vector, an adenovirus vector and a baculovirus transfer vector.

4. A host cell comprising the vector of claim 2.

5. The host cell of claim 4, which is eukaryotic.

6. The host cell of claim 5, which is mammalian.

7. The host cell of claim 6, which is selected from the group consisting of a COS cell, a CHO cell, a HeLa cell, a NIH/3T3 cell and an embryonic stem cell.

8. A method for producing an AGTR1 polypeptide, the method comprising: (a) culturing the host cell of claim 4 under conditions for protein expression; and (b) recovering said polypeptide.

9. The isolated polynucleotide of claim 1, which is a DNA molecule and comprises both the first and second nucleotide sequences and further comprises expression regulatory elements operably linked to the first nucleotide sequence.

10. A vector comprising the isolated polynucleotide of claim 9.

11. The vector of claim 10, which is selected from a vaccinia virus vector, a herpes virus vector, an adenovirus vector and a baculovirus transfer vector.

12. A host cell comprising the vector of claim 10.

13. The host cell of claim 12, which is eukaryotic.

14. The host cell of claim 13, which is mammalian.

15. The host cell of claim 14, which is selected from the group consisting of a COS cell, a CHO cell, a HeLa cell, a NIH/3T3 cell and an embryonic stem cell.

16. A method for producing AGTR1 polypeptide, the method comprising: (a) culturing the host cell of claim 12 under conditions for protein expression; and (b) recovering said polypeptide.

17. A collection of AGTR1 isogenes, which comprises the polynucleotide of claim 1 and at least one other polynucleotide selected from the group consisting of:
   i) a nucleotide sequence comprising nucleotides 11–1743 of SEQ ID NO:26 and having adenine at position 104, guanine at position 348, cytosine at position 1036, thymine at position 1074, cytosine at position 1470, adenine at position 1525, and thymine at position 1613;
   ii) a nucleotide sequence comprising nucleotides 11–1743 of SEQ ID NO:26 and having adenine at position 104, guanine at position 348, cytosine at position 1036, thymine at position 1074, cytosine at position 1470, guanine at position 1525, and guanine at position 1613;
   iii) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and guanine at position 1613;
   iv) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and thymine at position 1613;
   v) a nucleotide sequence comprising nucleotides 11–1743 of SEQ ID NO:26 and having thymine at position 104, guanine at position 348, cytosine at position 1036, thymine at position 1074, cytosine at position 1470, guanine at position 1525, and thymine at position 1613;
   vi) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and thymine at position 1613;
   vii) a nucleotide sequence comprising nucleotides 11–1743 of SEQ ID NO:26 and having thymine at position 1074, guanine at position 348, thymine at position 1036, cytosine at position 1074, cytosine at position 1470, adenine at position 1525, and thymine at position 1613;
   viii) a nucleotide sequence comprising nucleotides 11–1743 of SEQ ID NO:26 and having thymine at position 1074, guanine at position 348, thymine at position 1036, thymine at position 1074, cytosine at position 1470, adenine at position 1525, and thymine at position 1613; and
   ix) a nucleotide sequence comprising nucleotides 11–1743 of SEQ ID NO:26 and having thymine at position 104, thymine at position 348, thymine at position 1036, thymine at position 1074, cytosine at position 1470, adenine at position 1525, and thymine at position 1613.

18. The collection of AGTR1 isogenes of claim 17, wherein each isogene is stored in a separate container.

19. The collection of AGTR1 isogenes of claim 17, the selected polynucleotides comprising:
   i) a nucleotide sequence comprising nucleotides 11–1743 of SEQ ID NO:26 and having adenine at position 104, guanine at position 348, cytosine at position 1036, thymine at position 1074, cytosine at position 1470, adenine at position 1525, and thymine at position 1613;
   ii) a nucleotide sequence comprising nucleotides 11–1743 of SEQ ID: NO:26 and having thymine at position 104, guanine at position 348, cytosine at position 1036, thymine at position 1074, cytosine at position 1470, adenine at position 1525, and guanine at position 1613;
   iii) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and thymine at position 1613;
   iv) a nucleotide sequence comprising nucleotides 11–1743 of SEQ ID NO:26 and having thymine at position 104, guanine at position 348, cytosine at position 1036, thymine at position 1074, cytosine at position 1470, guanine at position 1525, and thymine at position 1613; and
   v) a nucleotide sequence comprising nucleotides 11–1743 of SEQ ID NO:26 and having thymine at position 104, guanine at position 348, thymine at position 1036, thymine at position 1074, cytosine at position 1470, adenine at position 1525, and thymine at position 1613.

20. The collection of AGTR1 isogenes of claim 19, wherein each isogene is stored in a separate container.

21. The collection of AGTR1 isogenes of claim 17, the selected polynucleotides comprising:
   i) a nucleotide sequence comprising nucleotides 11–1743 of SEQ ID NO:26 and having adenine at position 104, guanine at position 348, cytosine at position 1036, thymine at position 1074, cytosine at position 1470, adenine at position 1525, and thymine at position 1613; and
   ii) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and guanine at position 1613.

22. The collection of AGTR1 isogenes of claim 21, wherein each isogene is stored in a separate container.

23. The collection of AGTR1 isogenes of claim 17, the selected polynucleotides comprising:
   i) a nucleotide sequence comprising nucleotides 11–1743 of SEQ ID NO:26 and having adenine at position 104, guanine at position 348, cytosine at position 1036, thymine at position 1074, cytosine at position 1470, adenine at position 1525, and thymine at position 1613;
   ii) a nucleotide sequence comprising nucleotides 11–1743 of SEQ ID NO:26 and having adenine at position 104, guanine at position 348, cytosine at position 1036, thymine at position 1074, cytosine at position 1470, guanine at position 1525, and guanine at position 1613;
   iii) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and guanine at position 1613;
   iv) a nucleotide sequence comprising nucleotides 11–1743 of SEQ ID NO:26 and having thymine at position 104, guanine at position 348, cytosine at position 1036, thymine at position 1074, cytosine at position 1470, adenine at position 1525, and thymine at position 1613;
   v) a nucleotide sequence comprising nucleotides 11–1743 of SEQ ID NO:26 and having thymine at position 104, guanine at position 348, cytosine at position 1036, thymine at position 1074, cytosine at position 1470, guanine at position 1525, and thymine at position 1613;
   vi) a nucleotide sequence comprising nucleotides 11–1743 of SEQ ID NO.26 and having thymine at position 104, guanine at position 348, cytosine at position 1036, thymine at position 1074, cytosine at position 1470, adenine at position 1525, and thymine at position 1613;
   vii) a nucleotide sequence comprising nucleotides 11–1743 of SEQ ID NO:26 and having thymine at position 104, guanine at position 348, cytosine at position 1036, cytosine at position 1074, cytosine at position 1470, adenine at position 1525, and thymine at position 1613;
   viii) a nucleotide sequence comprising nucleotides 11–1743 of SEQ ID NO:26 and having thymine at position 104, guanine at position 348, thymine at position 1036, thymine at position 1074, cytosine at position 1470, adenine at position 1525, and thymine at position 1613; and
   ix) a nucleotide sequence comprising nucleotides 11–1743 of SEQ ID NO:26 and having thymine at position 104, thymine at position 348, thymine at position 1036, thymine at position 1074, cytosine at position 1470, adenine at position 1525, and thymine at position 1613.

24. The collection of AGTR1 isogenes of claim 23, wherein each isogene is stored in a separate container.

25. An isolated polynucleotide comprising a nucleotide sequence an angiotensin receptor 1 (AGTR1) coding sequence wherein the nucleotide sequence comprises SEQ ID NO:2 and having cytosine at position 573, thymine at position 611, cytosine at position 1007, and guanine at position 1062.

26. A vector comprising the isolated polynucleotide of claim 21.

27. The vector of claim 22, which is selected from a vaccinia virus vector, a herpes virus vector, an adenovirus vector and a baculovirus transfer vector.

28. A host cell comprising the vector of claim 22.

29. The host cell of claim 24, which is eukaryotic.

30. The host cell of claim 25, which is mammalian.

31. The host cell of claim 14, which is selected from the group consisting of a COS cell, a CHO cell, a HeLa cell, NIH3 cell and an embryonic stem cell.

32. A method for producing an AGTR1 polypeptide, the method comprising: (a) culturing the host cell of claim 28 under conditions for protein expression; and (b) recovering the polypeptide from the host cell culture.

* * * * *

UNITED STATES PATENT AND TRADEMARK OFFICE
CERTIFICATE OF CORRECTION

PATENT NO.     : 6,521,747 B2                                     Page 1 of 1
DATED          : February 18, 2003
INVENTOR(S)    : Alison E. Anastasio et al.

It is certified that error appears in the above-identified patent and that said Letters Patent is hereby corrected as shown below:

<u>Column 54,</u>
Line 50, replace "21" with -- 25 --.
Lines 51 and 54, replace "22" with -- 26 --.
Line 55, replace "24" with -- 28 --.
Line 56, replace "25" with -- 29 --.
Line 57, replace "14" with -- 30 --.

Signed and Sealed this

Second Day of March, 2004

JON W. DUDAS
*Acting Director of the United States Patent and Trademark Office*

SEQUENCE LISTING

```
<160> NUMBER OF SEQ ID NOS: 27

<210> SEQ ID NO 1
<211> LENGTH: 2632
<212> TYPE: DNA
<213> ORGANISM: Homo sapiens

<400> SEQUENCE: 1
ttaatgataa atgaattggt cctgcttacc tcaggaaaaa ctttcaagtc tttctgaaaa      60
actaatttaa ttcagtagta ttttctaaga tttaggttat gttttttaatc aatttggaaa    120 ccaagattta cttatagaaa aaaaggaaaa ggacctagat aggtttattc acatagaatc    180
ccaatttcac ttctctggat gataccattt tctacaaaag caattatgtt ctaaaattta    240
agtgtgcttt cttaggcttt atcagttcac agtgtttcct taagaaatat gatccagtat    300
tttttcctaa gactaaagtt gagttactac gtttatgact gagaaatgaa tgtttgttag    360
tttgtttgtt tacaataaga attttttctt taccatttta tttttatttt ccccaggtgt    420
atttgatata gtgtttgcaa caaattcgac ccaggtgatc aaaatgattc tcaactcttc    480
tactgaagat ggtattaaaa gaatccaaga tgattgtccc aaagctggaa ggcataatta    540
catatttgtc atgattccta ctttatacag tatcatcttt gtggtgggaa tatttggaaa    600
cagcttggtg gtgatagtca tttacttttta tatgaagctg aagactgtgg ccagtgtttt    660
tcttttgaat ttagcactgg ctgacttatg ctttttactg actttgccac tatgggctgt    720
ctacacagct atggaatacc gctggccctt tggcaattac ctatgtaaga ttgcttcagc    780
cagcgtcagt ttcaacctgt acgctagtgt gtttctactc acgtgtctca gcattgatcg    840
atacctggct attgttcacc caatgaagtc ccgccttcga cgcacaatgc ttgtagccaa    900
agtcacctgc atcatcattt ggctgctggc aggcttggcc agtttgccag ctataatcca    960
tcgaaatgta tttttcattg agaacaccaa tattacagtt tgtgctttcc attatgagtc   1020
ccaaaattca acccttccga tagggctggg cctgaccaaa aatatactgg gtttcctgtt   1080 tcctttttctg atcattctta caagttatac tcttatttgg aaggccctaa agaaggctta   1140
tgaaattcag aagaacaaac caagaaatga tgatattttt aagataatta tggcaattgt   1200
gcttttcttt ttctttttcct ggattcccca ccaaatattc acttttctgg atgtattgat   1260
tcaactaggc atcatacgtg actgtagaat tgcagatatt gtggacacgg ccatgcctat   1320
caccatttgt atagcttatt ttaacaattg cctgaatcct ctttttttatg gctttctggg   1380 gaaaaattt aaaagatatt ttctccagct tctaaaatat attcccccaa aagccaaatc   1440
ccactcaaac ctttcaacaa aaatgagcac gctttcctac cgcccctcag ataatgtaag   1500
ctcatccacc aagaagcctg caccatgttt tgaggttgag tgacatgttc gaaacctgtc   1560
```

-continued

| | |
|---|---|
| cataaagtaa ttttgtgaaa gaaggagcaa gagaacattc ctctgcagca cttcactacc | 1620 |
| aaatgagcat tagctacttt tcagaattga aggagaaaat gcattatgtg gactgaaccg | 1680 |
| acttttctaa agctctgaac aaaagctttt ctttccttt gcaacaagac aaagcaaagc | 1740 |
| cacattttgc attagacaga tgacggctgc tcgaagaaca atgtcagaaa ctcgatgaat | 1800 |
| gtgttgattt gagaaatttt actgacagaa atgcaatctc cctagcctgc ttttgtcctg | 1860 |
| ttattttta tttccacata aggtattta gaatatatta aatcgttaga ggagcaacag | 1920 |
| gagatgagag ttccagattg ttctgtccag tttccaaagg gcagtaaagt tttcgtgccg | 1980 |
| gttttcagct attagcaact gctgctacac ttgcacctgg tactgcacat tttgtacaaa | 2040 |
| gatatgctaa gcagtagtcg tcaagttgca gatcttttg tgaaattcaa cctgtgtctt | 2100 |
| ataggtttac actgccaaaa caatgcccgt aagatggctt atttgtataa tggtgttact | 2160 |
| aaagtcacat ataaagtta aactacttgt aaaggtgctg cactggtccc aagtagtagt | 2220 |
| gtcttcctag tatattagtt tgatttaata tctgagaagt gtatatagtt tgtggtaaaa | 2280 |
| agattatata tcataaagta tgccttctgt ttaaaaaaag tatatatcta cacatatata | 2340 |
| tatatgtata tctatatctc taaactgctg ttaattgatt aaaatctggc aaagttatat | 2400 |
| ttactttaaa ataaaataat tttattgcaa tgtatttatc ttcattactt aaaatagatg | 2460 |
| ctaatttatt ttaaaataag actaccttga atgagtatga atatattttt atttaaattt | 2520 |
| tgatacaact gatagtttaa tactattggt tatagatttt ttatcctgac attgaaaagt | 2580 |
| taaagaaaaa acattttgtt ctactgcatg tcatggaata aacacatcgt tt | 2632 |

<210> SEQ ID NO 2
<211> LENGTH: 1080
<212> TYPE: DNA
<213> ORGANISM: Homo sapiens

<400> SEQUENCE: 2

| | |
|---|---|
| atgattctca actcttctac tgaagatggt attaaaagaa tccaagatga ttgtcccaaa | 60 |
| gctggaaggc ataattacat atttgtcatg attcctactt tatacagtat catctttgtg | 120 |
| gtgggaatat ttggaaacag cttggtggtg atagtcattt acttttatat gaagctgaag | 180 |
| actgtggcca gtgttttct tttgaattta gcactggctg acttatgctt tttactgact | 240 |
| ttgccactat gggctgtcta cacagctatg gaataccgct ggccctttgg caattaccta | 300 |
| tgtaagattg cttcagccag cgtcagtttc aacctgtacg ctagtgtgtt tctactcacg | 360 |
| tgtctcagca ttgatcgata cctggctatt gttcacccaa tgaagtcccg ccttcgacgc | 420 |
| acaatgcttg tagccaaagt cacctgcatc atcatttggg ctgctggcagg cttggccagt | 480 |
| ttgccagcta taatccatcg aaatgtattt ttcattgaga acaccaatat tacagtttgt | 540 |
| gctttccatt atgagtccca aaattcaacc cttccgatag ggctgggcct gaccaaaaat | 600 |
| atactgggtt tcctgttcc ttttctgatc attcttacaa gttatactct tatttggaag | 660 |
| gccctaaaga aggcttatga aattcagaag aacaaaccaa gaaatgatga tattttaag | 720 |
| ataattatgg caattgtgct tttctttttc ttttcctgga ttccccacca aatattcact | 780 |
| tttctggatg tattgattca actaggcatc atacgtgact gtagaattgc agatattgtg | 840 |
| gacacggcca tgcctatcac catttgtata gcttatttta acaattgcct gaatcctctt | 900 |
| ttttatggct ttctggggaa aaatttaaa agatattttc tccagcttct aaaatatatt | 960 |
| cccccaaaag ccaaatccca ctcaaacctt tcaacaaaaa tgagcacgct ttcctaccgc | 1020 |
| ccctcagata atgtaagctc atccaccaag aagcctgcac catgttttga ggttgagtga | 1080 |

<210> SEQ ID NO 3
<211> LENGTH: 359
<212> TYPE: PRT
<213> ORGANISM: Homo sapiens

<400> SEQUENCE: 3

```
Met Ile Leu Asn Ser Ser Thr Glu Asp Gly Ile Lys Arg Ile Gln Asp
 1               5                  10                  15

Asp Cys Pro Lys Ala Gly Arg His Asn Tyr Ile Phe Val Met Ile Pro
                20                  25                  30

Thr Leu Tyr Ser Ile Ile Phe Val Val Gly Ile Phe Gly Asn Ser Leu
            35                  40                  45

Val Val Ile Val Ile Tyr Phe Tyr Met Lys Leu Lys Thr Val Ala Ser
        50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
145                 150                 155                 160

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
        290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
            340                 345                 350

Ala Pro Cys Phe Glu Val Glu
            355
```

-continued

```
<210> SEQ ID NO 4
<211> LENGTH: 15
<212> TYPE: DNA
<213> ORGANISM: Homo sapiens

<400> SEQUENCE: 4
ttatgttwtt aatca                                                    15

<210> SEQ ID NO 5
<211> LENGTH: 15
<212> TYPE: DNA
<213> ORGANISM: Homo sapiens

<400> SEQUENCE: 5
gagaaatkaa tgttt                                                    15

<210> SEQ ID NO 6
<211> LENGTH: 15
<212> TYPE: DNA
<213> ORGANISM: Homo sapiens

<400> SEQUENCE: 6
ctgggttycc tgttt                                                    15

<210> SEQ ID NO 7
<211> LENGTH: 15
<212> TYPE: DNA
<213> ORGANISM: Homo sapiens

<400> SEQUENCE: 7
atgagcaygc tttcc                                                    15

<210> SEQ ID NO 8
<211> LENGTH: 15
<212> TYPE: DNA
<213> ORGANISM: Homo sapiens

<400> SEQUENCE: 8
tttaggttat gttwt                                                    15

<210> SEQ ID NO 9
<211> LENGTH: 15
<212> TYPE: DNA
<213> ORGANISM: Homo sapiens

<400> SEQUENCE: 9
ccaaattgat taawa                                                    15

<210> SEQ ID NO 10
<211> LENGTH: 15
<212> TYPE: DNA
<213> ORGANISM: Homo sapiens

<400> SEQUENCE: 10
atgactgaga aatka                                                    15

<210> SEQ ID NO 11
<211> LENGTH: 15
<212> TYPE: DNA
<213> ORGANISM: Homo sapiens

<400> SEQUENCE: 11
actaacaaac attma                                                    15
```

```
<210> SEQ ID NO 12
<211> LENGTH: 15
<212> TYPE: DNA
<213> ORGANISM: Homo sapiens

<400> SEQUENCE: 12
aatatactgg gttyc                                                    15

<210> SEQ ID NO 13
<211> LENGTH: 15
<212> TYPE: DNA
<213> ORGANISM: Homo sapiens

<400> SEQUENCE: 13
aaaaggaaac aggra                                                    15

<210> SEQ ID NO 14
<211> LENGTH: 15
<212> TYPE: DNA
<213> ORGANISM: Homo sapiens

<400> SEQUENCE: 14
acaaaaatga gcayg                                                    15

<210> SEQ ID NO 15
<211> LENGTH: 15
<212> TYPE: DNA
<213> ORGANISM: Homo sapiens

<400> SEQUENCE: 15
gcggtaggaa agcrt                                                    15

<210> SEQ ID NO 16
<211> LENGTH: 10
<212> TYPE: DNA
<213> ORGANISM: Homo sapiens

<400> SEQUENCE: 16
aggttatgtt                                                          10

<210> SEQ ID NO 17
<211> LENGTH: 10
<212> TYPE: DNA
<213> ORGANISM: Homo sapiens

<400> SEQUENCE: 17
aattgattaa                                                          10

<210> SEQ ID NO 18
<211> LENGTH: 10
<212> TYPE: DNA
<213> ORGANISM: Homo sapiens

<400> SEQUENCE: 18
actgagaaat                                                          10

<210> SEQ ID NO 19
<211> LENGTH: 10
<212> TYPE: DNA
<213> ORGANISM: Homo sapiens

<400> SEQUENCE: 19
aacaaacatt                                                          10
```

```
<210> SEQ ID NO 20
<211> LENGTH: 10
<212> TYPE: DNA
<213> ORGANISM: Homo sapiens

<400> SEQUENCE: 20
atactgggtt                                                              10

<210> SEQ ID NO 21
<211> LENGTH: 10
<212> TYPE: DNA
<213> ORGANISM: Homo sapiens

<400> SEQUENCE: 21
aggaaacagg                                                              10

<210> SEQ ID NO 22
<211> LENGTH: 10
<212> TYPE: DNA
<213> ORGANISM: Homo sapiens

<400> SEQUENCE: 22
aaaatgagca                                                              10

<210> SEQ ID NO 23
<211> LENGTH: 10
<212> TYPE: DNA
<213> ORGANISM: Homo sapiens

<400> SEQUENCE: 23
gtaggaaagc                                                              10

<210> SEQ ID NO 24
<211> LENGTH: 18
<212> TYPE: DNA
<213> ORGANISM: Homo sapiens

<400> SEQUENCE: 24
tgtaaaacga cggccagt                                                     18

<210> SEQ ID NO 25
<211> LENGTH: 19
<212> TYPE: DNA
<213> ORGANISM: Homo sapiens

<400> SEQUENCE: 25
aggaaacagc tatgaccat                                                    19

<210> SEQ ID NO 26
<211> LENGTH: 2632
<212> TYPE: DNA
<213> ORGANISM: Homo sapiens
<220> FEATURE:
<221> NAME/KEY: allele
<222> LOCATION: (104)
<223> OTHER INFORMATION: PS1: polymorphic base T or A
<221> NAME/KEY: allele
<222> LOCATION: (348)
<223> OTHER INFORMATION: PS2: polymorphic base G or T
<221> NAME/KEY: allele
<222> LOCATION: (1036)
<223> OTHER INFORMATION: PS3: polymorphic base T or C
<221> NAME/KEY: allele
<222> LOCATION: (1074)
<223> OTHER INFORMATION: PS4: polymorphic base T or C
```

```
<221> NAME/KEY: allele
<222> LOCATION: (1470)
<223> OTHER INFORMATION: PS5: polymorphic base C or T
<221> NAME/KEY: allele
<222> LOCATION: (1525)
<223> OTHER INFORMATION: PS6: polymorphic base A or G
<221> NAME/KEY: allele
<222> LOCATION: (1613)
<223> OTHER INFORMATION: PS7: polymorphic base T or G

<400> SEQUENCE: 26
ttaatgataa atgaattggt cctgcttacc tcaggaaaaa ctttcaagtc tttctgaaaa      60
actaatttaa ttcagtagta ttttctaaga tttaggttat gttwttaatc aatttggaaa     120
ccaagattta cttatagaaa aaaggaaaa ggacctagat aggtttattc acatagaatc     180
ccaatttcac ttctctggat gataccattt tctacaaaag caattatgtt ctaaaattta     240
agtgtgcttt cttaggcttt atcagttcac agtgtttcct taagaaatat gatccagtat     300
tttttcctaa gactaaagtt gagttactac gtttatgact gagaaatkaa tgtttgttag     360
tttgtttgtt tacaataaga attttttctt taccatttta tttttatttt ccccaggtgt     420
atttgatata gtgtttgcaa caaattcgac ccaggtgatc aaaatgattc tcaactcttc     480
tactgaagat ggtattaaaa gaatccaaga tgattgtccc aaagctggaa ggcataatta     540
catatttgtc atgattccta ctttatacag tatcatcttt gtggtgggaa tatttggaaa     600
cagcttggtg gtgatagtca tttacttta tatgaagctg aagactgtgg ccagtgtttt     660
tcttttgaat ttagcactgg ctgacttatg ctttttactg actttgccac tatgggctgt     720
ctacacagct atggaatacc gctggccctt tggcaattac ctatgtaaga ttgcttcagc     780
cagcgtcagt ttcaacctgt acgctagtgt gtttctactc acgtgtctca gcattgatcg     840
atacctggct attgttcacc caatgaagtc ccgccttcga cgcacaatgc ttgtagccaa     900
agtcacctgc atcatcattt ggctgctggc aggcttggcc agtttgccag ctataatcca     960
tcgaaatgta ttttcattg agaacaccaa tattacagtt tgtgctttcc attatgagtc    1020
ccaaaattca accctyccga tagggctggg cctgaccaaa aatatactgg gttycctgtt    1080
tccttttctg atcattctta caagttatac tcttatttgg aaggccctaa agaaggctta    1140
tgaaattcag aagaacaaac caagaaatga tgatattttt aagataatta tggcaattgt    1200
gctttttcttt ttctttttcct ggattcccca ccaaatattc acttttctgg atgtattgat    1260
tcaactaggc atcatacgtg actgtagaat tgcagatatt gtggacacgg ccatgcctat    1320
caccatttgt atagcttatt ttaacaattg cctgaatcct cttttttatg gctttctggg    1380
gaaaaaattt aaaagatatt ttctccagct tctaaaatat attcccccaa aagccaaatc    1440
ccactcaaac ctttcaacaa aaatgagcay gctttcctac cgcccctcag ataatgtaag    1500
ctcatccacc aagaagcctg caccrtgttt tgaggttgag tgacatgttc gaaacctgtc    1560
cataaagtaa ttttgtgaaa gaaggagcaa gagaacattc ctctgcagca ctkcactacc    1620
aaatgagcat tagctacttt tcagaattga aggagaaaat gcattatgtg gactgaaccg    1680
acttttctaa agctctgaac aaaagctttt ctttccttt gcaacaagac aaagcaaagc    1740
cacattttgc attagacaga tgacggctgc tcgaagaaca atgtcagaaa ctcgatgaat    1800
gtgttgattt gagaaatttt actgacagaa atgcaatctc cctagcctgc ttttgtcctg    1860
ttatttttta tttccacata aaggtattta gaatatatta aatcgttaga ggagcaacag    1920
gagatgagag ttccagattg ttctgtccag tttccaaagg gcagtaaagt tttcgtgccg    1980
gttttcagct attagcaact gctgctacac ttgcacctgg tactgcacat tttgtacaaa    2040
```

```
gatatgctaa gcagtagtcg tcaagttgca gatcttttttg tgaaattcaa cctgtgtctt    2100
ataggtttac actgccaaaa caatgcccgt aagatggctt atttgtataa tggtgttact    2160
aaagtcacat ataaaagtta aactacttgt aaaggtgctg cactggtccc aagtagtagt    2220
gtcttcctag tatattagtt tgatttaata tctgagaagt gtatatagtt tgtggtaaaa    2280
agattatata tcataaagta tgccttctgt ttaaaaaaag tatatatcta cacatatata    2340
tatatgtata tctatatctc taaactgctg ttaattgatt aaaatctggc aaagttatat    2400
ttactttaaa ataaaataat tttattgcaa tgtatttatc ttcattactt aaaatagatg    2460
ctaatttatt ttaaaataag actaccttga atgagtatga atatatttttt atttaaattt    2520 tgatacaact gatagtttaa tactattggt tatagatttt ttatcctgac attgaaaagt    2580
taaagaaaaa acattttgtt ctactgcatg tcatggaata aacacatcgt tt           2632
```

<210> SEQ ID NO 27
<211> LENGTH: 780
<212> TYPE: DNA
<213> ORGANISM: Homo sapiens
<220> FEATURE:
<221> NAME/KEY: allele
<222> LOCATION: (30)
<223> OTHER INFORMATION: PS1: polymorphic base T or A
<221> NAME/KEY:
<222> LOCATION: (61)..(120)
<223> OTHER INFORMATION: nucleotides represent sequence between PS
<221> NAME/KEY: allele
<222> LOCATION: (150)
<223> OTHER INFORMATION: PS2: polymorphic base G or T
<221> NAME/KEY:
<222> LOCATION: (181)..(240)
<223> OTHER INFORMATION: nucleotides represent sequence between PS
<221> NAME/KEY: allele
<222> LOCATION: (270)
<223> OTHER INFORMATION: PS3: polymorphic base T or C
<221> NAME/KEY:
<222> LOCATION: (301)..(360)
<223> OTHER INFORMATION: nucleotides represent sequence between PS
<221> NAME/KEY: allele
<222> LOCATION: (390)
<223> OTHER INFORMATION: PS4: polymorphic base T or C
<221> NAME/KEY:
<222> LOCATION: (421)..(480)
<223> OTHER INFORMATION: nucleotides represent sequence between PS
<221> NAME/KEY: allele
<222> LOCATION: (510)
<223> OTHER INFORMATION: PS5: polymorphic base C or T
<221> NAME/KEY:
<222> LOCATION: (541)..(600)
<223> OTHER INFORMATION: nucleotides represent sequence between PS
<221> NAME/KEY: allele
<222> LOCATION: (630)
<223> OTHER INFORMATION: PS6: polymorphic base A or G
<221> NAME/KEY:
<222> LOCATION: (661)..(720)
<223> OTHER INFORMATION: nucleotides represent sequence between PS
<221> NAME/KEY: allele
<222> LOCATION: (750)
<223> OTHER INFORMATION: PS7: polymorphic base T or G

<400> SEQUENCE: 27

```
gtagtatttt ctaagattta ggttatgttw ttaatcaatt tggaaaccaa gatttactta      60
nnnnnnnnnn nnnnnnnnnn nnnnnnnnnn nnnnnnnnnn nnnnnnnnnn nnnnnnnnnn     120
ttgagttact acgtttatga ctgagaaatk aatgtttgtt agtttgtttg tttacaataa     180
nnnnnnnnnn nnnnnnnnnn nnnnnnnnnn nnnnnnnnnn nnnnnnnnnn nnnnnnnnnn     240
ttccattatg agtcccaaaa ttcaaccctty ccgatagggc tgggcctgac caaaaatata    300
```

-continued

```
nnnnnnnnnn nnnnnnnnnn nnnnnnnnnn nnnnnnnnnn nnnnnnnnnn nnnnnnnnnn    360
gctgggcctg accaaaaata tactgggtty cctgtttcct tttctgatca ttcttacaag    420
nnnnnnnnnn nnnnnnnnnn nnnnnnnnnn nnnnnnnnnn nnnnnnnnnn nnnnnnnnnn    480
ccactcaaac ctttcaacaa aaatgagcay gctttcctac cgcccctcag ataatgtaag    540
nnnnnnnnnn nnnnnnnnnn nnnnnnnnnn nnnnnnnnnn nnnnnnnnnn nnnnnnnnnn    600
gtaagctcat ccaccaagaa gcctgcaccr tgttttgagg ttgagtgaca tgttcgaaac    660
nnnnnnnnnn nnnnnnnnnn nnnnnnnnnn nnnnnnnnnn nnnnnnnnnn nnnnnnnnnn    720
ggagcaagag aacattcctc tgcagcactk cactaccaaa tgagcattag ctacttttca    780
```